(12) United States Patent
Takimiya et al.

(10) Patent No.: US 9,564,604 B2
(45) Date of Patent: Feb. 7, 2017

(54) FUSED POLYCYCLIC AROMATIC COMPOUNDS, ORGANIC SEMICONDUCTOR MATERIAL AND THIN FILM INCLUDING THE SAME, AND METHOD FOR PRODUCING AN ORGANIC SEMICONDUCTOR DEVICE

(71) Applicant: Nippon Kayaku Kabushiki Kaisha, Tokyo (JP)

(72) Inventors: Kazuo Takimiya, Higashihiroshima (JP); Shoji Shinamura, Tokyo (JP); Masahiro Hamada, Tokyo (JP); Yuichi Sadamitsu, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/436,187

(22) PCT Filed: Oct. 17, 2013

(86) PCT No.: PCT/JP2013/078210
§ 371 (c)(1),
(2) Date: Apr. 16, 2015

(87) PCT Pub. No.: WO2014/061745
PCT Pub. Date: Apr. 24, 2014

(65) Prior Publication Data
US 2015/0303383 A1 Oct. 22, 2015

(30) Foreign Application Priority Data
Oct. 18, 2012 (JP) .................... 2012-230469

(51) Int. Cl.
*H01L 51/00* (2006.01)
*C07D 495/04* (2006.01)
(Continued)

(52) U.S. Cl.
CPC ......... *H01L 51/0074* (2013.01); *C07D 493/04* (2013.01); *C07D 495/04* (2013.01);
(Continued)

(58) Field of Classification Search
CPC ............................ H01L 51/00; C07D 495/04
See application file for complete search history.

(56) References Cited

U.S. PATENT DOCUMENTS

2008/0171228 A1 7/2008 Chen et al.
2011/0095270 A1* 4/2011 Meng .................. C07D 493/04
257/40

(Continued)

FOREIGN PATENT DOCUMENTS

CN 101222024 A 7/2008
CN 102239140 A 11/2011
(Continued)

OTHER PUBLICATIONS

International Search Report/Written Opinion mailed Dec. 10, 2013 in corresponding PCT application No. PCT/JP2013/078210.
(Continued)

*Primary Examiner* — Caleb Henry
(74) *Attorney, Agent, or Firm* — Nields, Lemack & Frame, LLC

(57) ABSTRACT

The present invention provides a fused aromatic compound represented by general formula (1) or general formula (2):
(Continued)

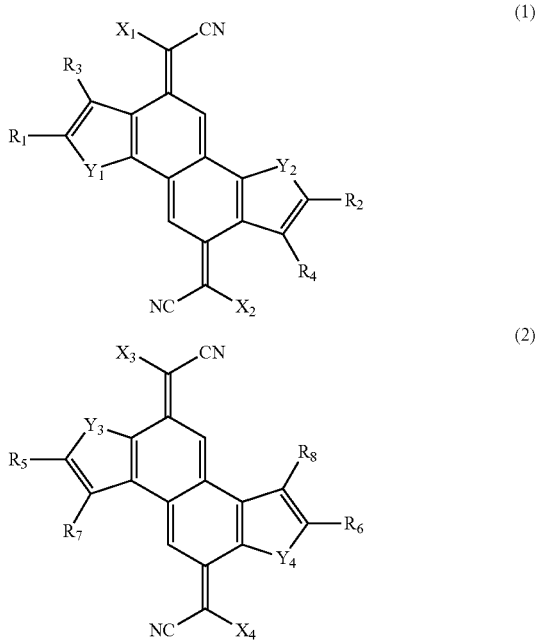

wherein $R_1$ to $R_8$ each independently represent an atom or a functional group selected from the group consisting of a hydrogen atom, a halogen atom, a hydrocarbon oxy group, an aromatic hydrocarbon group, an aliphatic hydrocarbon group, an alicyclic hydrocarbon group, an ester group, an acyl group, a cyano group, and a substituted silyl group, $X_1$ to $X_4$ each independently represent a cyano group, an ester group, or an acyl group, and $Y_1$ to $Y_4$ each independently represent an oxygen atom, a sulfur atom, or a selenium atom.

16 Claims, 4 Drawing Sheets

(51) Int. Cl.
C07D 493/04 (2006.01)
C07D 517/04 (2006.01)
H01L 51/05 (2006.01)

(52) U.S. Cl.
CPC ........ *C07D 517/04* (2013.01); *H01L 51/0051* (2013.01); *H01L 51/0541* (2013.01); *H01L 51/0545* (2013.01); *H01L 51/0558* (2013.01)

(56) References Cited

U.S. PATENT DOCUMENTS

| | | | | |
|---|---|---|---|---|
| 2011/0284827 | A1 | 11/2011 | Morishita et al. | |
| 2012/0305899 | A1* | 12/2012 | Taki | C08G 61/126 257/40 |
| 2013/0247992 | A1* | 9/2013 | Drees | H01L 51/0043 136/263 |
| 2014/0061616 | A1* | 3/2014 | Sunagawa | C07D 495/04 257/40 |
| 2014/0128618 | A1* | 5/2014 | Hayoz | C07D 519/00 548/453 |
| 2014/0217329 | A1* | 8/2014 | Hayoz | C09B 23/148 252/500 |
| 2015/0112081 | A1* | 4/2015 | Takimiya | C07D 513/04 548/110 |
| 2015/0132887 | A1* | 5/2015 | Welker | C09B 57/00 438/99 |
| 2015/0284504 | A1* | 10/2015 | Cheng | C08G 61/126 526/240 |
| 2016/0013428 | A1* | 1/2016 | Takimiya | C07D 495/04 438/99 |

FOREIGN PATENT DOCUMENTS

| | | |
|---|---|---|
| CN | 102666643 A | 9/2012 |
| EP | 2068379 A1 | 6/2009 |
| JP | 10-135481 A | 5/1998 |
| JP | 2005-255889 A | 9/2005 |
| JP | 2008-244430 A | 10/2008 |
| JP | 2009-200263 A | 9/2009 |
| JP | 2009-242339 A | 10/2009 |
| JP | 2011-165747 A | 8/2011 |
| JP | 2012-131938 A | 7/2012 |
| WO | 2008/032715 A1 | 3/2008 |
| WO | 2010/064655 A1 | 6/2010 |
| WO | 2010/098326 A1 | 9/2010 |

OTHER PUBLICATIONS

J. Am. Chem. Soc, 2007, vol. 129, No. 38, pp. 11684-11685, "Solution-Processible n-Channel Organic Field-Effect Transistors Based on Dicyanomethylene-Substituted Terthienoquinoid Derivative", Handa, et al.
Chemistry Letters, 2009, vol. 38, No. 6, pp. 568-569, "Alkylated 2,6-Bis(dicyanonnethylene)-2,6-dihydrobenzo[1,2-b:4,5-b']dithiophenes:New Soluble n-Channel Organic Semiconductors for Air-stable OFETs", Kashiki, et al.
J. Am. Chem. Soc., 1996, vol. 118, pp. 11331-11332, "n-Channel Organic Transistor Materials Based on Naphthalene Frameworks", Laquindanum, et al.
Chem. Rev., 2010, vol. 110, pp. 890-931, "C—H Activation for the Construction of C—B Bonds", Mkhalid, et al.
Chem. Commun., 2012, vol. 48, pp. 5671-5673, "Angular-shaped naphthodifurans, naphtho[1,2-b;5,6-b']- and naphtho[2,1-b;6,5-b']-difuran: are they isoelectronic with chrysene?", Nakano, et al.
J. Am. Chem. Soc., 2002, vol. 124, pp. 4184-4185, "A Pi-Stacking Terthiophene-Based Quinodinnethane is an n-Channel Conductor in a Thin Film Transistor", Pappenfus, et al.
J. Am. Chem. Soc., 2011, vol. 133, pp. 5024-5035, "Linear- and Angular-Shaped Naphthodithiophenes: Selective Synthesis, Properties, and Application to Organic Field-Effect Transistors", Shinamura, et al.
J. Org. Chem., 2010, vol. 75, pp. 1228-1234, "Synthesis, Properties, Crystal Structures, and Semiconductor Characteristics of Naphtho[1,2-b:5,6-b']dithiophene and -diselenophene Derivatives", Shinamura, et al.
Synthetic Metals, 1989, vol. 30, No. 3, pp. 401-402, "Synthesis of 1,2,3,6,7,8-Hexahydro-10,10,11,11-Tetracyano-4,9-Pyrenoquinodimethane", Yamaguchi, et al.
J. Org. Chem., 1994, vol. 59, pp. 3077-3081, "Novel Electron Acceptors Bearing a Heteroquinonoid System. 4.1 Syntheses, Properties, and Charge-Transfer Complexes of 2,7-Bis(dicyanomethylene)-2,7-dihydrobenzo[2,1-b:3,4-b']dithiophene, 2,7-Bis(dicyanomethylene)-2,7-dihydrobenzo[1,2-b:4,3-b']dithiophene, and 2,6-Bis(dicyanomethylene)-2,6-dihydrobenzo[1,2-b:4,5-b']dithiophene", Yoshida, et al.
J. Org. Chem., 2002, vol. 67, pp. 1905-1909, "Synthesis of 2,3-Disubstituted Benzo[b]thiophenes via Palladium-Catalyzed Coupling and Electrophilic Cyclization of Terminal Acetylenes", Yue, et al.
J.Org. Chem., 2005, vol. 70, pp. 10292-10296, "Synthesis of 2,3-Disubstituted Benzo[b]furans by the Palladium-Catalyzed Coupling of o-Iodoanisoles and Terminal Alkynes, Followed by Electrophilic Cyclization", Yue, et al.

(56) References Cited

OTHER PUBLICATIONS

Chinese communication, with English translation, dated Apr. 5, 2016 in corresponding Chinese patent application No. 201380054760.4.

* cited by examiner

FUSED POLYCYCLIC AROMATIC COMPOUNDS, ORGANIC SEMICONDUCTOR MATERIAL AND THIN FILM INCLUDING THE SAME, AND METHOD FOR PRODUCING AN ORGANIC SEMICONDUCTOR DEVICE

TECHNICAL FIELD

The present invention relates to a fused polycyclic aromatic compound, to an organic semiconductor material and an organic semiconductor device including the same, and to a method for producing the fused polycyclic aromatic compound and a method for producing the organic semiconductor device. More specifically, the present invention relates to a fused polycyclic aromatic compound that enables stable n-type transistor operation in the atmosphere and an organic semiconductor material and an organic semiconductor device including the same, and to a method for producing the fused polycyclic aromatic compound and a method for producing the organic semiconductor device.

BACKGROUND ART

In recent years, thin film devices that include organic semiconductor materials such as organic EL devices, organic FET (field-effect transistor) devices, and organic thin-film photoelectric conversion devices have attracted attention, and have started putting into practical use. Of the fundamental physical characteristics of organic semiconductor materials for use in these thin film devices, carrier mobility and an on/off ratio are important. For example, in organic EL devices, carrier mobility, which influences charge transport efficiency, is important for highly efficient light emission and driving at low voltages. Also, in organic FET devices, carrier mobility and on/off ratios, which directly influence switching speed and the performance of a device to be driven, are important for putting organic FET devices into practical use.

Also, in order to make efficient use of the characteristics of organic semiconductor materials in these thin film devices, stable driving in the atmosphere is important. Stable driving in the atmosphere would make operations under an inert atmosphere and sealing and the like unnecessary. Thus, production processes can be simplified, and costs for equipment required for production can be greatly reduced.

Conventionally, in organic semiconductor materials, as with inorganic semiconductor materials, organic semiconductor materials for use in p-type (i.e., hole-transporting) transistors (referred to as "p-type material" hereinbelow) and organic semiconductor materials for use in n-type (i.e., electron-transporting) transistors (referred to as "n-type material" hereinbelow) are known. For example, in order to fabricate logical circuits such as CMOS (complementary metal oxide semiconductors), p-type materials and n-type materials have been required.

Up to now, a lot of research on p-type materials has been conducted, and materials that have high performance and are driven stably in the atmosphere have been reported. In contrast, as for n-type materials, researches have not greatly advanced, and limited materials are stably driven in the atmosphere.

One example of the n-type materials driven stably in the atmosphere is compounds having a quinoid structure. Of these, thienoquinoid compounds have been widely investigated, and high-performance materials such as oligothiophene quinoid materials and benzodithiophene quinoid materials have been developed (Patent Literatures 1 to 2 and Non-patent Literatures 1 to 3). On the other hand, although compounds having a benzoquinoid structure may have a possibility of being an n-type material having stability in the atmosphere and high performance, very few researches have been made on FET materials having a benzoquinoid structure.

Patent Literature 3 and Non-patent Literature 4 describe an organic semiconductor material that has a structure represented by the chemical formula:

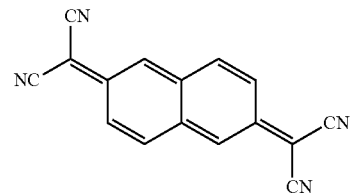 [SMILES: N#CC(C#N)=c1ccc2cc(=C(C#N)C#N)ccc2c1]

and can be used for organic FET devices. They show that the material has higher electron mobility and stability under atmospheric conditions than tetracyanoquinodimethane. However, the material exhibits high off current, thereby decreasing an on/off ratio, and thus may not constitute a practical transistor.

CITATION LIST

Patent Literature

Patent Literature 1 WO 2008-032715
Patent Literature 2 JP 2009-242339 A
Patent Literature 3 JP 10-135481 A Non Patent Literature Non Patent Literature 1 J. Am. Chem. Soc., 2002, 124, 4184
Non Patent Literature 2 J. Am. Chem. Soc., 2007, 129, 11684
Non Patent Literature 3 Chem. Lett., 2009, 38, 568
Non Patent Literature 4 J. Am. Chem. Soc., 1996, 118, 11331

SUMMARY OF INVENTION

Technical Problem

An object of the present invention is to provide an n-type semiconductor material that is stable in the atmosphere and has a large on/off ratio.

Solution to Problem

In order to solve the above-described problem, the present inventors have developed a novel heterocyclic derivative, and furthermore investigated the potential thereof for organic electronics devices, thereby completing the present invention.

That is, the present invention is as follows.

[1] A fused polycyclic aromatic compound represented by general formula (1) or (2):

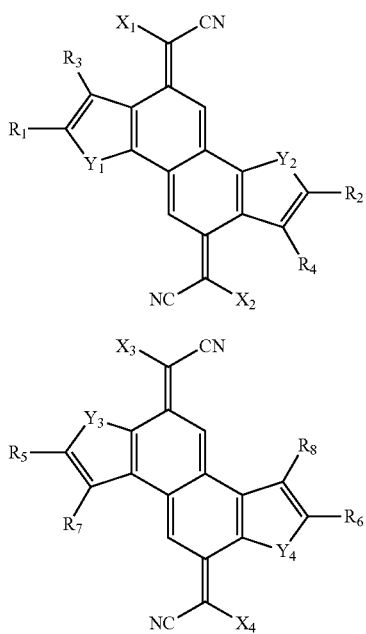

wherein $R_1$ to $R_8$ each independently represent an atom or a functional group selected from the group consisting of a hydrogen atom, a halogen atom, a hydrocarbon oxy group, an aromatic hydrocarbon group, an aliphatic hydrocarbon group, an alicyclic hydrocarbon group, an ester group, an acyl group, a cyano group, and a substituted silyl group, $X_1$ to $X_4$ each independently represent a cyano group, an ester group, or an acyl group, and $Y_1$ to $Y_4$ each independently represent an oxygen atom, a sulfur atom, or a selenium atom.

[2] The fused polycyclic aromatic compound according to [1], wherein $X_1$ and $X_2$, or $X_3$ and $X_4$ are a cyano group.

[3] The fused polycyclic aromatic compound according to [1] or [2], wherein $R_3$, $R_4$, $R_7$, and $R_8$ are all a hydrogen atom.

[4] The fused polycyclic aromatic compound according to any one of [1] to [3], wherein $Y_1$ and $Y_2$, or $Y_3$ and $Y_4$ are a sulfur atom.

[5] The fused polycyclic aromatic compound according to any one of [1] to [4], wherein $R_1$, $R_2$, $R_5$, and $R_6$ are each independently an aromatic hydrocarbon group or an aliphatic hydrocarbon group having 1 to 30 carbon atoms.

[6] The fused polycyclic aromatic compound according to [5], wherein the $R_1$, $R_2$, $R_5$, and $R_6$ are each independently a linear chain or branched chain alkyl group having 1 to 30 carbon atoms.

[7] The fused polycyclic aromatic compound according to any one of [1] to [4], wherein the $R_1$, $R_2$, $R_5$, and $R_6$ are each independently a trimethylsilyl group, a triethylsilyl group, or a triisopropylsilyl group.

[8] The fused polycyclic aromatic compound according to any one of [1] to [4], wherein the $R_1$, $R_2$, $R_5$, and $R_6$ are all a hydrogen atom.

[9] An organic semiconductor material comprising the fused polycyclic aromatic compound according to any one of [1] to [8].

[10] The organic semiconductor material according to [9], wherein the organic semiconductor material is an n-type semiconductor material.

[11] A composition for forming an organic semiconductor comprising the fused polycyclic aromatic compound according to any one of [1] to [8] and an organic solvent.

[12] The composition for forming an organic semiconductor according to [11], wherein the content of the fused polycyclic aromatic compound is in a range of 0.01% by weight or more and 10% by weight or less relative to the total amount of the composition for forming an organic semiconductor.

[13] A thin film comprising the fused polycyclic aromatic compound according to any one of [1] to [8].

[14] An organic semiconductor device comprising the thin film according to [13].

[15] The organic semiconductor device according to [14], wherein the device is an organic transistor device.

[16] A method for producing an organic semiconductor device comprising a step of depositing the fused polycyclic aromatic compound according to any one of [1] to [8] on a substrate via a solution process.

[17] A method for producing an organic semiconductor device comprising a step of depositing the fused polycyclic aromatic compound according to any one of [1] to [8] on a substrate via a vacuum process.

Advantageous Effects of Invention

The present invention relates to a novel compound which is an n-type semiconductor stably driven in the atmosphere and having a high on/off ratio. The semiconductor can be used to provide organic electronic devices.

DESCRIPTION OF EMBODIMENTS

Figure 1:
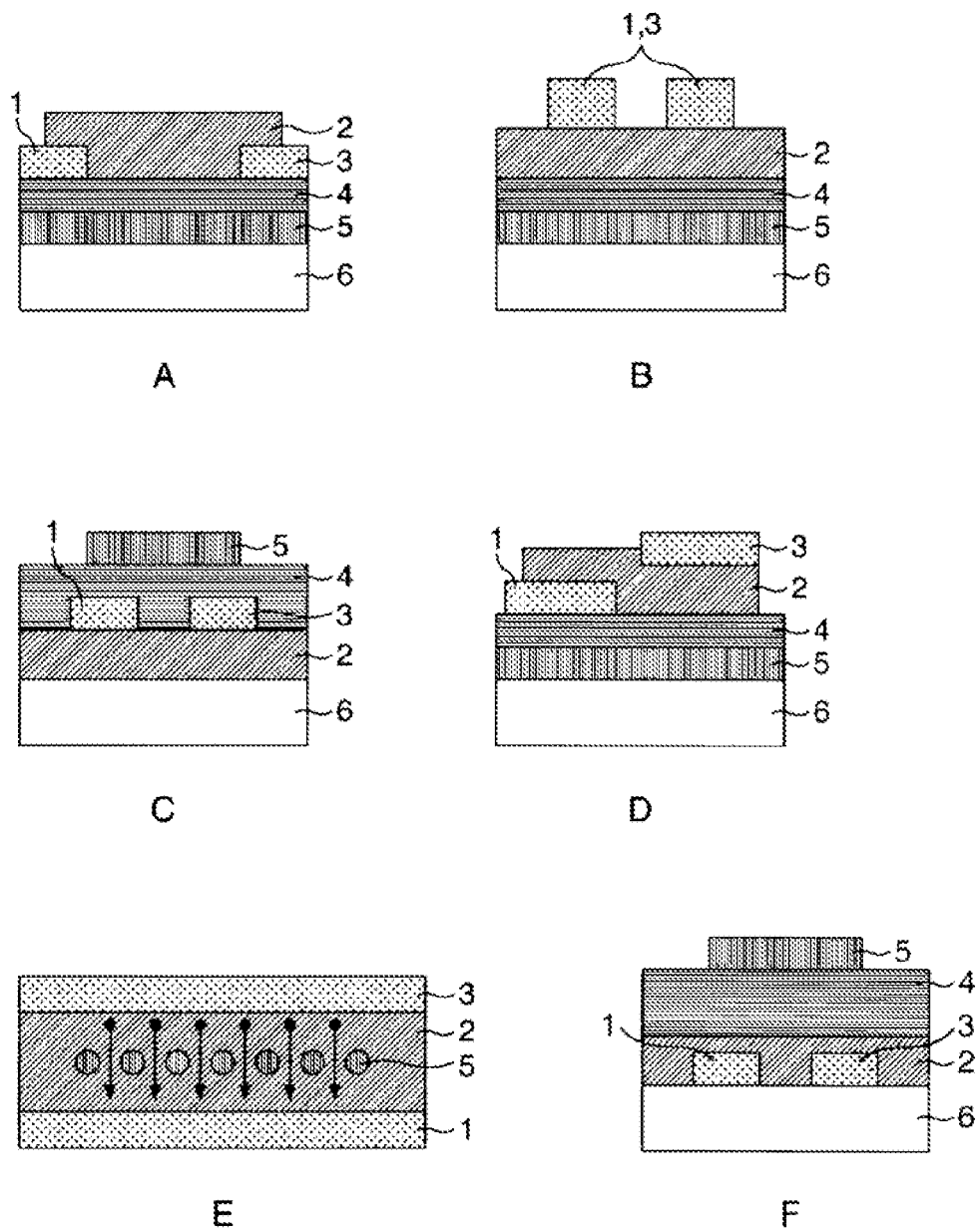
FIG. 1 is a schematic view showing the structure of a thin film transistor according to an exemplary aspect of the present invention.

Hereinafter, the present invention will be described in detail.

A fused polycyclic aromatic compound represented by the following general formula (1) or (2) will be described.

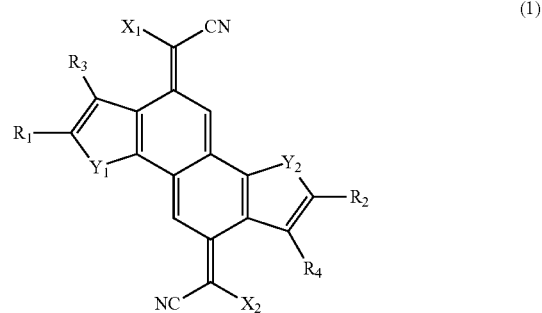

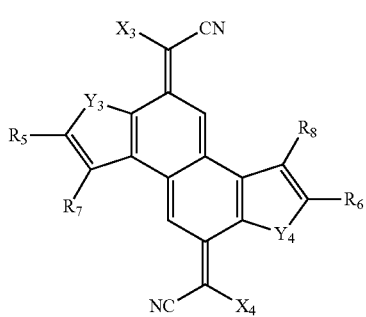

(2)

In general formula (1) or (2), $R_1$ to $R_8$ each independently represent an atom or a functional group selected from the group consisting of a hydrogen atom, a halogen atom, a hydrocarbon oxy group, an aromatic hydrocarbon group, an aliphatic hydrocarbon group, an alicyclic hydrocarbon group, an ester group, an acyl group, a cyano group, and substituted silyl group, and $X_1$ to $X_4$ each independently represent a cyano group, an ester group, or an acyl group. More specifically, $R_1$ to $R_8$ each independently represent an atom or a functional group selected from the group consisting of a hydrogen atom, a halogen atom, a hydrocarbon oxy group, an aromatic hydrocarbon group, an aliphatic hydrocarbon group, an alicyclic hydrocarbon group, an ester group, an acyl group, a silyl group, and a cyano group. The Rs are independent from each other in terms of their positions, number, and types of substituents. In the case where there are two or more substituents, two or more types of substituents can coexist.

The above-described halogen atom includes a fluorine atom, a chlorine atom, a bromine atom, and an iodine atom.

The aliphatic hydrocarbon group includes saturated or unsaturated linear or branched chain hydrocarbon groups, which have preferably 1 to 30, more preferably 1 to 20, even more preferably 6 to 12, and particularly preferably 8 to 12 carbon atoms. The saturated or unsaturated linear or branched chain aliphatic hydrocarbon group includes a methyl group, an ethyl group, a propyl group, an isopropyl group, a n-butyl group, an iso-butyl group, an allyl group, a t-butyl group, a n-pentyl group, a n-hexyl group, a n-octyl group, a n-decyl group, a n-dodecyl group, a n-tridecyl group, a n-tetradecyl group, a n-cetyl group, a n-heptadecyl group, and a n-butenyl group. The hydrocarbon group is preferably a saturated linear chain alkyl group. Particularly, a n-octyl group, a n-decyl group, or a n-dodecyl group is preferred.

The alicyclic hydrocarbon group includes saturated or unsaturated cyclic hydrocarbon groups. Examples of the cyclic hydrocarbon group include cyclic hydrocarbon groups having 3 to 12 carbon atoms, such as a cyclohexyl group, a cyclopentyl group, an adamantyl group, and a norbornyl group.

The aromatic hydrocarbon group include a phenyl group, a naphthyl group, an anthryl group, a phenanthryl group, a pyrenyl group, and a benzopyrenyl group, and additionally include heterocyclic groups such as a pyridyl group, a pyrazyl group, a pyrimidyl group, a quinolyl group, an isoquinolyl group, a pyrrolyl group, an indolenyl group, an imidazolyl group, a carbazolyl group, a thienyl group, a furyl group, a pyranyl group, and a pyridonyl group, and fused heterocyclic groups such as a benzoquinolyl group, an anthraquinolyl group, a benzothienyl group, and a benzofuryl group. Of these, a phenyl group, a naphthyl group, a pyridyl group, and a thienyl group are preferred, and a phenyl group is particularly preferred.

The hydrocarbon oxy group includes hydrocarbon oxy groups including the above-described aliphatic hydrocarbon groups.

The ester group includes ester groups including the above-described aliphatic hydrocarbon groups, and the acyl group includes acyl groups including the above-described aliphatic hydrocarbon groups.

The substituted silyl group includes silyl groups substituted with two or more alkyl groups having 1 to 4 carbon atoms, such as a trimethylsilyl group, a triethylsilyl group, a t-butyl dimethylsilyl group, and a triisopropylsilyl group. The substituted silyl group is preferably a trimethylsilyl group or a triisopropylsilyl group.

$X_1$ to $X_4$ each independently represent a cyano group, an ester group, or an acyl group. The ester group and the acyl group respectively include ester groups and acyl groups including the above-described aliphatic hydrocarbon groups. Of these, compounds of formulas (1) and (2) wherein $X_1$ and $X_2$, or $X_3$ and $X_4$ are a cyano group are preferred.

$Y_1$ to $Y_4$ each independently represent an oxygen atom, a sulfur atom, or a selenium atom. Of these, compounds of formulas (1) and (2) wherein $Y_1$ and $Y_2$, or $Y_3$ and $Y_4$ are sulfur atoms are preferred.

A compound of general formula (1) can be obtained by a reaction of a compound of general formula (3) with a compound of general formula (5) as in the following scheme.

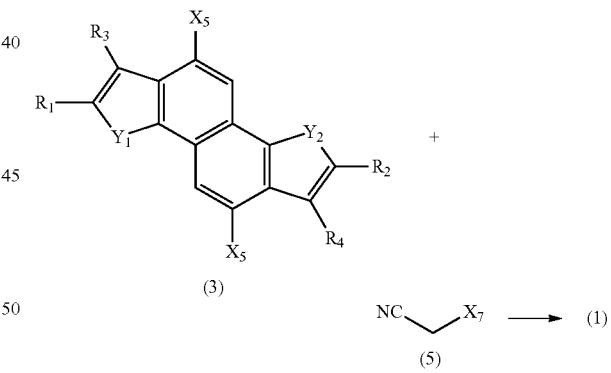

$Y_1$ and $Y_2$, and $R_1$ to $R_4$ in general formula (3) are as previously described. $X_5$ represents a halogen atom, which includes a fluorine atom, a chlorine atom, a bromine atom, and an iodine atom. The halogen atom is preferably a bromine atom or an iodine atom. $X_7$ represents a cyano group, an ester group, or an acyl group. The ester group and acyl group respectively include ester groups and acyl groups having the above-described aliphatic hydrocarbon group(s). Among them, a cyano group is preferred.

A compound of general formula (2) can be obtained by a reaction of a compound of general formula (4) with a compound of general formula (5) as in the following scheme.

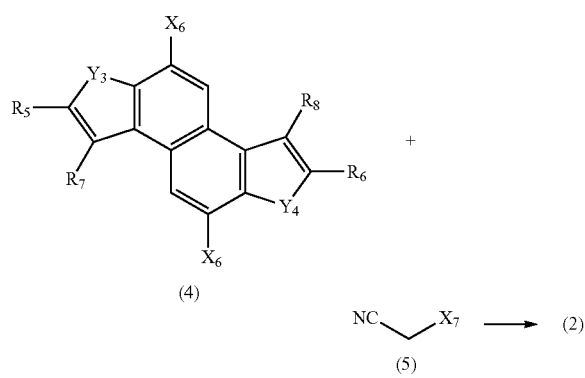

(4)

NC—X$_7$ (5) → (2)

Y$_3$ and Y$_4$, R$_5$ to R$_8$, and X$_7$ in general formula (4) are as previously described. X$_6$ represents a halogen atom, which includes a fluorine atom, a chlorine atom, a bromine atom, and an iodine atom. The halogen atom is preferably a bromine atom or an iodine atom.

A fused polycyclic aromatic compound represented by general formula (1) or (2) according to the present invention can be synthesized, for instance, in accordance with the method described in J. Org. Chem., 1994, 59, 3077. Specifically, a compound of general formula (1) or (2) can be obtained by a reaction of a compound of general formula (3) or (4) with a compound of general formula (5) in a solvent or in the absence of a solvent, with a catalyst in the presence of a base.

The catalyst used in such a reaction preferably includes palladium catalysts such as PdCl$_2$(PPh$_3$)$_2$, Pd(PPh$_3$)$_4$, Pd(OAc)$_2$, and PdCl$_2$. The amount of these catalysts used is, although not particularly limited, usually 0.001 to 1 mole, preferably 0.01 to 0.5 moles, and more preferably 0.05 moles to 0.3 moles per mole of a compound of general formula (3) or (4). Also, phosphine ligands such as triphenylphosphine, 1,1'-bis(diphenylphosphino)ferrocene (dppf), 1,2-bis(diphenylphosphino)ethane (dppe), and 1,3-bis(diphenylphosphino)propane (dppp) can be used, and dppf is preferably used.

The base includes inorganic bases such as potassium carbonate, sodium carbonate, potassium hydride, and sodium hydride, and sodium hydride is preferably used. The amount of these bases are, although not particularly limited as long as the amount is sufficient for the reaction, usually 0.1 to 100 moles, preferably 0.5 to 50 moles, and more preferably 1 to 10 moles per mole of a compound of general formula (3) or (4).

In the case where the reaction is conducted in a solvent, ethers such as diethyl ether, anisole, and tetrahydrofuran; amides such as dimethylacetamide and dimethylformamide; nitriles such as acetonitrile, propionitrile, and benzonitrile; and alcohols such as methanol, ethanol, and butanol can be used as a reaction solvent. Of these, ether solvents such as tetrahydrofuran are preferred. The amount of these solvents is, although not particularly limited, of the order of 1 to 10000 moles per mole of a compound(s) of general formula (3) or (4).

The reaction temperature is preferably −50° C. to 300° C. The reaction temperature may be varied within this range as required, and is more preferably 0° C. to 250° C. and even more preferably 10° C. to 200° C. In general, the reaction is preferably completed in a short period. Specifically, the reaction time is preferably 10 minutes to 1000 hours, more preferably 30 minutes to 100 hours, and even more preferably 30 minutes to 24 hours. The reaction temperature and the amounts of catalysts, bases, and solvents used are preferably adjusted so as to complete the reaction in a short period.

Upon request, a substance of interest can be isolated or purified from the reaction mixture by a known isolation or purification method. When used as organic semiconductors, compounds having high purity are often required. Such high purity compounds can be obtained by known methods such as recrystallization, column chromatography, and vacuum sublimation purification. These purification methods may be conducted in combination, as required.

Heterocyclic compounds represented by general formula (3) or (4) of the present invention can be produced by conventional known methods.

That is, compounds represented by general formula (3) or (4) can be produced by halogenation of a compound represented by general formula (6) or (7), for instance, in accordance with Chem. Rev. 2010, 110, 890.

Compounds represented by general formula (6) or (7) can be synthesized in accordance with J. Org. Chem., 2010, 75, 1228, J. Am. Chem. Soc., 2011, 133, 5024, Chem. Commun., 2012, 48, 5671, or synthesized by cyclization of a compound represented by general formula (8) or (9) in accordance with J. Org. Chem. 2002, 67, 1905., J. Org. Chem. 2005, 70, 10292, followed by cross-coupling reaction such as Suzuki coupling, Negishi coupling, and Kumada coupling.

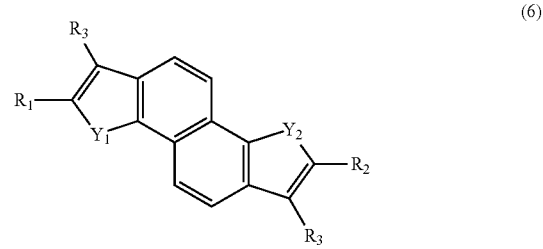

(6)

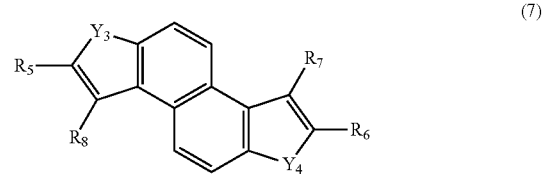

(7)

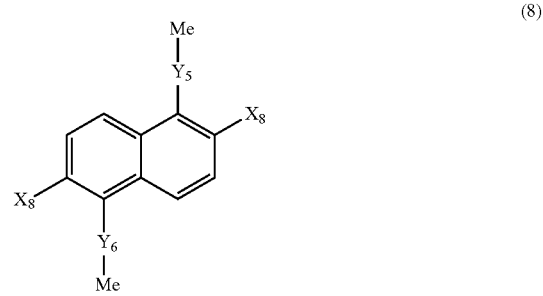

(8)

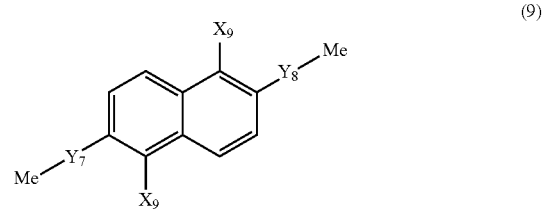

(9)

Y$_1$ to Y$_4$ and R$_1$ to R$_8$ in general formula (6) or (7) are as previously described. X$_8$ and X$_9$ in general formula (8) or (9)

represent a halogen atom, which includes a fluorine atom, a chlorine atom, a bromine atom, and an iodine atom. The halogen atom is preferably a bromine atom or an iodine atom. Also, $Y_5$ to $Y_8$ each independently represent an oxygen atom, a sulfur atom, or a selenium atom, preferably a sulfur atom.

Exemplary compounds represented by general formula (1) according to the present invention will be shown below. Table 1 shows compounds of the formula wherein $X_1$ and $X_2$ are a cyano group and, $Y_1$ and $Y_2$ are a sulfur atom. However, the present invention is not intended to be limited to these.

TABLE 1

| | $R_1$ | $R_2$ | $R_3$ | $R_4$ |
|---|---|---|---|---|
| 101 | H | H | H | H |
| 102 | $CH_3$ | H | H | H |
| 103 | $C_2H_5$ | $C_2H_5$ | H | H |
| 104 | n-$C_3H_7$ | n-$C_3H_7$ | H | H |
| 105 | iso-$C_3H_7$ | iso-$C_3H_7$ | H | H |
| 106 | n-$C_4H_9$ | n-$C_4H_9$ | H | H |
| 107 | iso-$C_4H_9$ | iso-$C_4H_9$ | H | H |
| 108 | tert-$C_4H_9$ | tert-$C_4H_9$ | H | H |
| 109 | n-$C_6H_{13}$ | n-$C_6H_{13}$ | H | H |
| 110 | n-$C_8H_{17}$ | n-$C_8H_{17}$ | H | H |
| 111 | n-$C_{10}H_{21}$ | n-$C_{10}H_{21}$ | H | H |
| 112 | n-$C_{12}H_{25}$ | n-$C_{12}H_{25}$ | H | H |
| 113 | n-$C_{14}H_{29}$ | n-$C_{14}H_{29}$ | H | H |
| 114 | n-$C_{16}H_{33}$ | n-$C_{16}H_{33}$ | H | H |
| 115 | n-$C_{18}H_{37}$ | n-$C_{18}H_{37}$ | H | H |
| 116 | n-$C_{20}H_{41}$ | n-$C_{20}H_{41}$ | H | H |
| 117 | 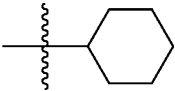 [SMILES: *C1CCCCC1] | 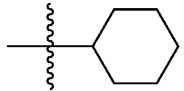 [SMILES: *C1CCCCC1] | H | H |
| 118 | 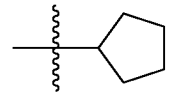 | 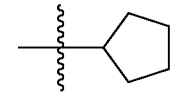 [SMILES: *C1CCCC1] | H | H |
| 119 | 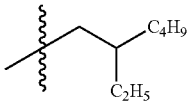 | 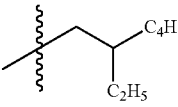 | H | H |
| 120 | 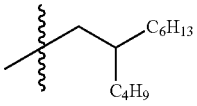 | 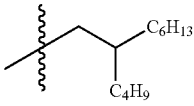 | H | H |
| 121 | 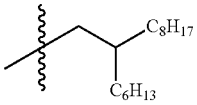 | 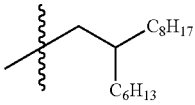 | H | H |
| 122 | 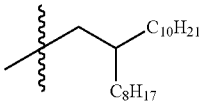 | 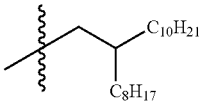 | H | H |
| 123 | 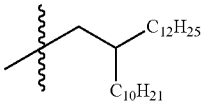 | 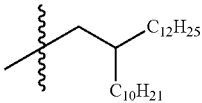 | H | H |
| 124 | 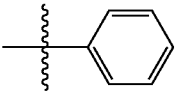 | 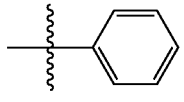 | H | H |
| 125 | 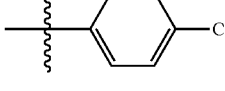 | 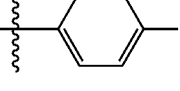 | H | H |

TABLE 1-continued

| | R₁ | R₂ | R₃ | R₄ |
|---|---|---|---|---|
| 126 | -C₆H₄-C₅H₁₁ | -C₆H₄-C₅H₁₁ | H | H |
| 127 | -C₆H₄-C₈H₁₇ | -C₆H₄-C₈H₁₇ | H | H |
| 128 | 2-thienyl | 2-thienyl | H | H |
| 129 | 5-C₈H₁₇-thien-2-yl | 5-C₈H₁₇-thien-2-yl | H | H |
| 130 | 5-C₁₂H₂₅-thien-2-yl | 5-C₁₂H₂₅-thien-2-yl | H | H |
| 131 | 2-pyridyl | 2-pyridyl | H | H |
| 132 | 2-naphthyl | 2-naphthyl | H | H |
| 133 | 1-naphthyl | 1-naphthyl | H | H |
| 134 | Si(CH₃)₃ | Si(CH₃)₃ | H | H |
| 135 | Si(C₂H₅)₃ | Si(C₂H₅)₃ | H | H |
| 136 | Si(iso-C₃H₉)₃ | Si(iso-C₃H₉)₃ | H | H |
| 137 | OCH₃ | OCH₃ | H | H |
| 138 | OC₈H₁₇ | OC₈H₁₇ | H | H |
| 139 | OC₁₂H₂₅ | OC₁₂H₂₅ | H | H |
| 140 | CO₂CH₃ | CO₂CH₃ | H | H |
| 141 | CO₂C₈H₁₇ | CO₂C₈H₁₇ | H | H |
| 142 | CO₂C₁₂H₂₅ | CO₂C₁₂H₂₅ | H | H |
| 143 | COCH₃ | COCH₃ | H | H |
| 144 | COC₃H₁₇ | COC₃H₁₇ | H | H |
| 145 | COC₁₂H₂₅ | COC₁₂H₂₅ | H | H |
| 146 | CN | CN | H | H |
| 147 | F | F | H | H |
| 148 | Cl | Cl | H | H |
| 149 | H | H | n-C₈H₁₇ | n-C₈H₁₇ |
| 150 | n-C₈H₁₇ | n-C₈H₁₇ | n-C₈H₁₇ | n-C₈H₁₇ |
| 151 | H | H | phenyl | phenyl |
| 152 | phenyl | phenyl | phenyl | phenyl |

TABLE 1-continued
| | R₁ | R₂ | R₃ | R₄ |
|---|---|---|---|---|
| 153 | (phenyl) | n-C₈H₁₇ | H | H |
| 154 | (4-C₅H₁₁-phenyl) | n-C₈H₁₇ | H | H |
A broken line means a atomic bonding
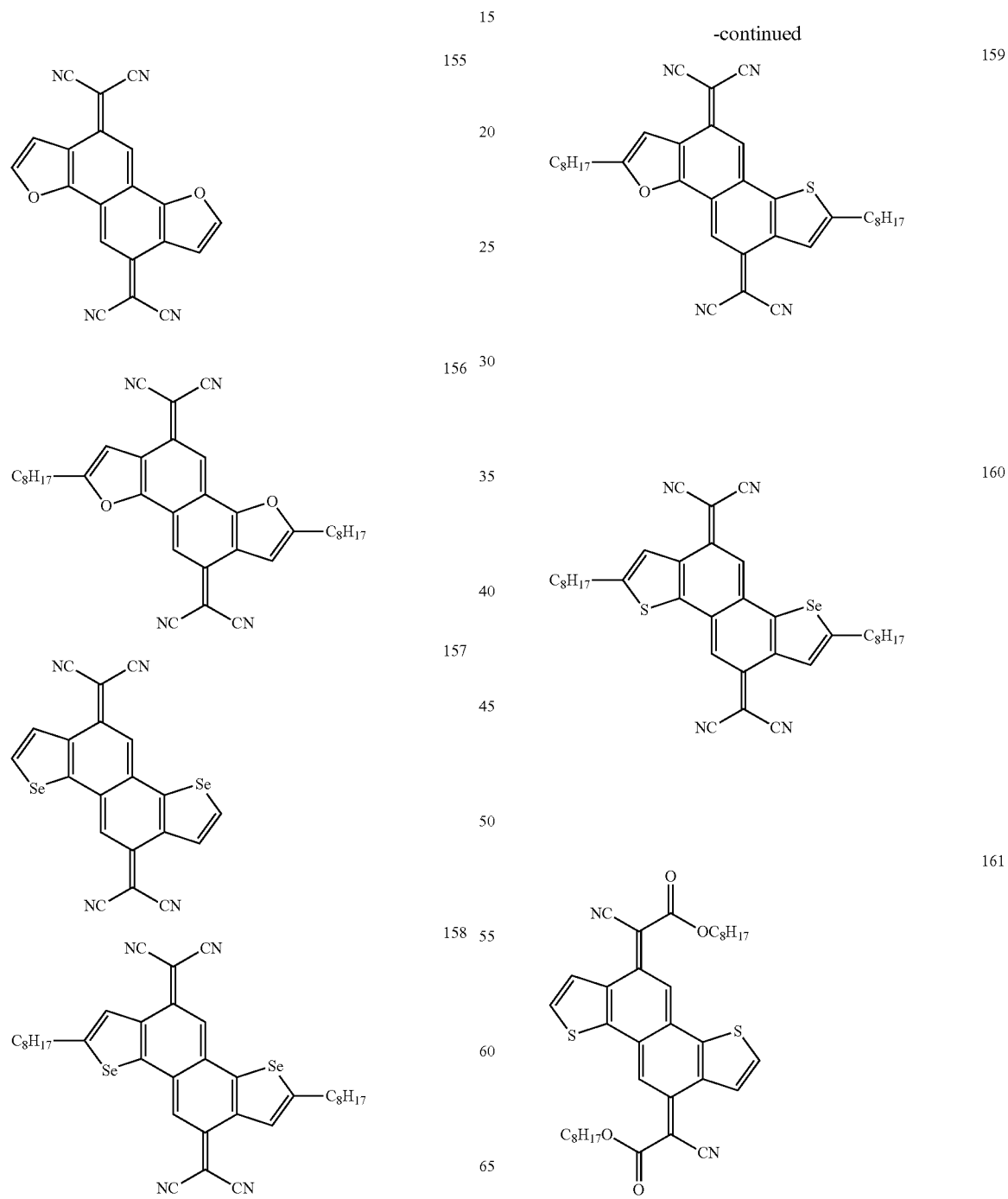

-continued

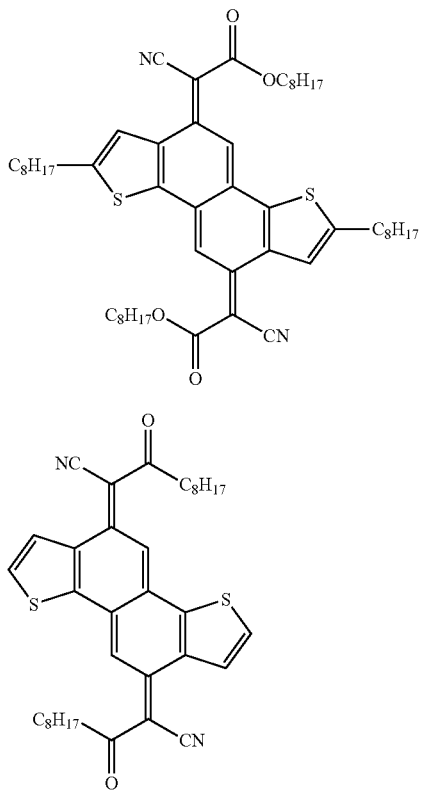

162

163

-continued

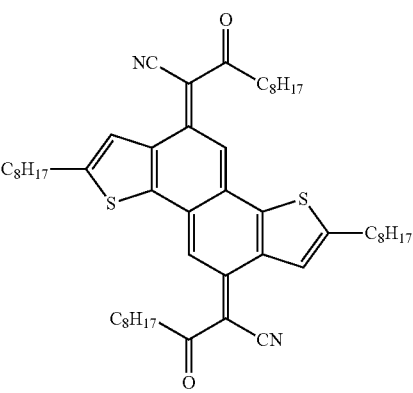

164

Exemplary compounds represented by general formula (2) according to the present invention will be shown below. Table 2 shows compounds of the formula wherein $X_3$ and $X_4$ are a cyano group, and $Y_3$ and $Y_4$ are a sulfur atom. However, the present invention is not intended to be limited to these.

TABLE 2

|     | $R_1$ | $R_2$ | $R_3$ | $R_4$ |
|-----|-------|-------|-------|-------|
| 201 | H | H | H | H |
| 202 | $CH_3$ | H | H | H |
| 203 | $C_2H_5$ | $C_2H_5$ | H | H |
| 204 | n-$C_3H_7$ | n-$C_3H_7$ | H | H |
| 205 | iso-$C_3H_7$ | iso-$C_3H_7$ | H | H |
| 206 | n-$C_4H_9$ | n-$C_4H_9$ | H | H |
| 207 | iso-$C_4H_9$ | iso-$C_4H_9$ | H | H |
| 208 | tert-$C_4H_9$ | tert-$C_4H_9$ | H | H |
| 209 | n-$C_6H_{13}$ | n-$C_6H_{13}$ | H | H |
| 210 | n-$C_8H_{17}$ | n-$C_8H_{17}$ | H | H |
| 211 | n-$C_{10}H_{21}$ | n-$C_{10}H_{21}$ | H | H |
| 212 | n-$C_{12}H_{25}$ | n-$C_{12}H_{25}$ | H | H |
| 213 | n-$C_{14}H_{29}$ | n-$C_{14}H_{29}$ | H | H |
| 214 | n-$C_{16}H_{33}$ | n-$C_{16}H_{33}$ | H | H |
| 215 | n-$C_{18}H_{37}$ | n-$C_{18}H_{37}$ | H | H |
| 216 | n-$C_{20}H_{41}$ | n-$C_{20}H_{41}$ | H | H |
| 217 | —cyclohexyl | —cyclohexyl | H | H |
| 218 | —cyclopentyl | —cyclopentyl | H | H |
| 219 | —CH(C$_2$H$_5$)CH$_2$—C$_4$H$_9$ branched | —CH(C$_2$H$_5$)CH$_2$—C$_4$H$_9$ branched | H | H |

TABLE 2-continued
| | R₁ | R₂ | R₃ | R₄ |
|---|---|---|---|---|
| 220 | 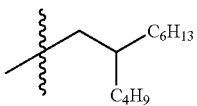 | 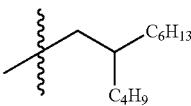 | H | H |
| 221 | 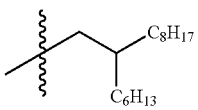 | 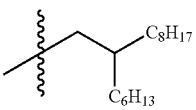 | H | H |
| 222 | 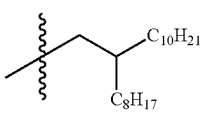 | 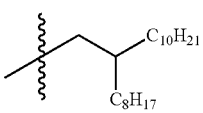 | H | H |
| 223 | 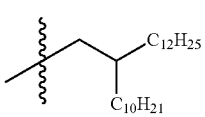 | 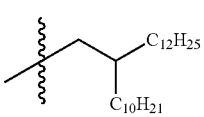 | H | H |
| 224 | 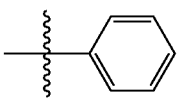 [SMILES: *c1ccccc1] | 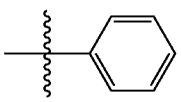 [SMILES: *c1ccccc1] | H | H |
| 225 | 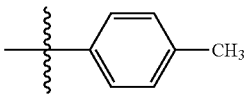 [SMILES: *c1ccc(C)cc1] | 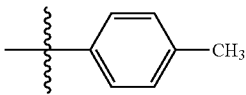 [SMILES: *c1ccc(C)cc1] | H | H |
| 226 | 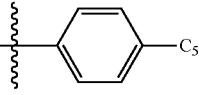 | 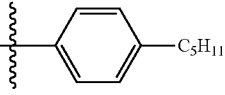 | H | H |
| 227 | 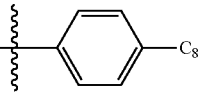 | 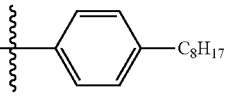 | H | H |
| 228 | 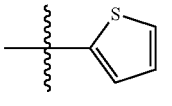 | 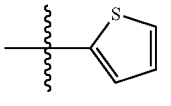 [SMILES: *c1cccs1] | H | H |
| 229 | 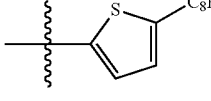 | 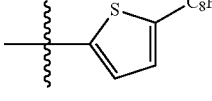 | H | H |
| 230 | 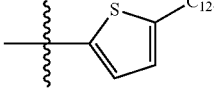 | 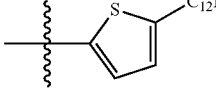 | H | H |
| 231 | 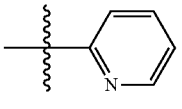 [SMILES: *c1ccccn1] | 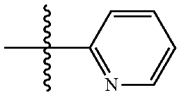 [SMILES: *c1ccccn1] | H | H |
| 232 | 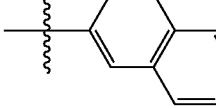 | 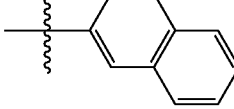 | H | H |

TABLE 2-continued

| | $R_1$ | $R_2$ | $R_3$ | $R_4$ |
|---|---|---|---|---|
| 233 | 1-naphthyl | 1-naphthyl | H | H |
| 234 | Si(CH$_3$)$_3$ | Si(CH$_3$)$_3$ | H | H |
| 235 | Si(C$_2$H$_5$)$_3$ | Si(C$_2$H$_5$)$_3$ | H | H |
| 236 | Si(iso-C$_3$H$_9$)$_3$ | Si(iso-C$_3$H$_9$)$_3$ | H | H |
| 237 | OCH$_3$ | OCH$_3$ | H | H |
| 238 | OC$_8$H$_{17}$ | OC$_8$H$_{17}$ | H | H |
| 239 | OC$_{12}$H$_{25}$ | OC$_{12}$H$_{25}$ | H | H |
| 240 | CO$_2$CH$_3$ | CO$_2$CH$_3$ | H | H |
| 241 | CO$_2$C$_8$H$_{17}$ | CO$_2$C$_8$H$_{17}$ | H | H |
| 242 | CO$_2$C$_{12}$H$_{25}$ | CO$_2$C$_{12}$H$_{25}$ | H | H |
| 243 | COCH$_3$ | COCH$_3$ | H | H |
| 244 | COC$_8$H$_{17}$ | COC$_8$H$_{17}$ | H | H |
| 245 | COC$_{12}$H$_{25}$ | COC$_{12}$H$_{25}$ | H | H |
| 246 | CN | CN | H | H |
| 247 | F | F | H | H |
| 248 | Cl | Cl | H | H |
| 249 | H | H | n-C$_8$H$_{17}$ | n-C$_8$H$_{17}$ |
| 250 | n-C$_8$H$_{17}$ | n-C$_8$H$_{17}$ | n-C$_8$H$_{17}$ | n-C$_8$H$_{17}$ |
| 251 | H | H | phenyl | phenyl |
| 252 | phenyl | phenyl | phenyl | phenyl |
| 253 | phenyl | n-C$_8$H$_{17}$ | H | H |
| 254 | 4-pentylphenyl | n-C$_8$H$_{17}$ | H | H |

A broken line means a atomic bonding

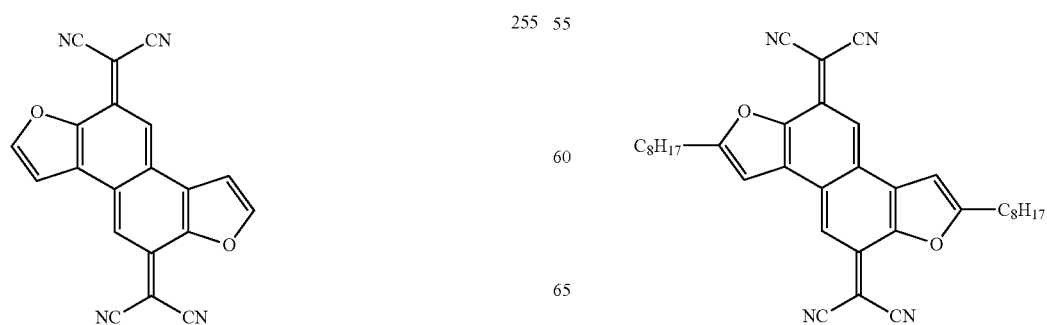

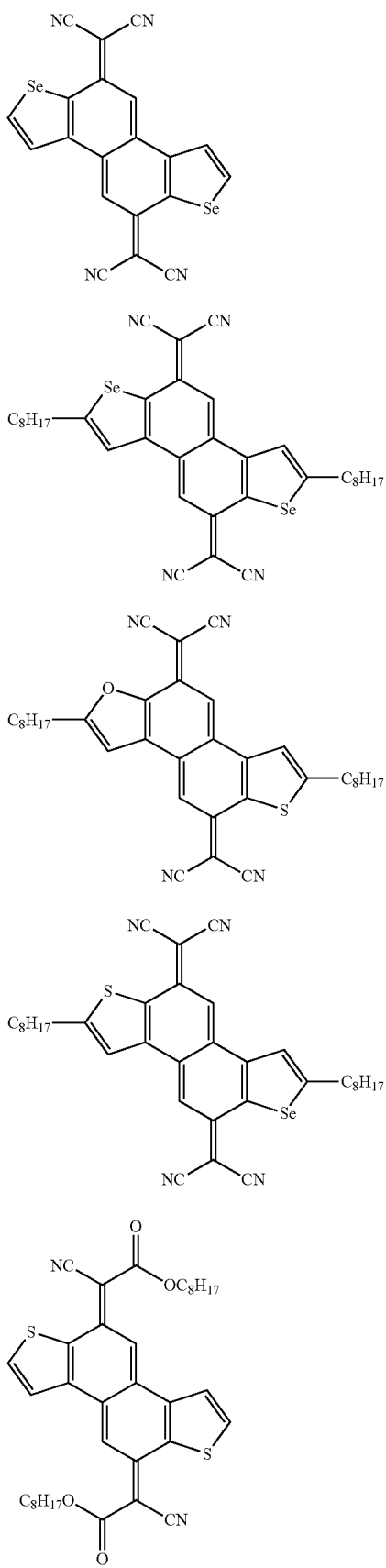

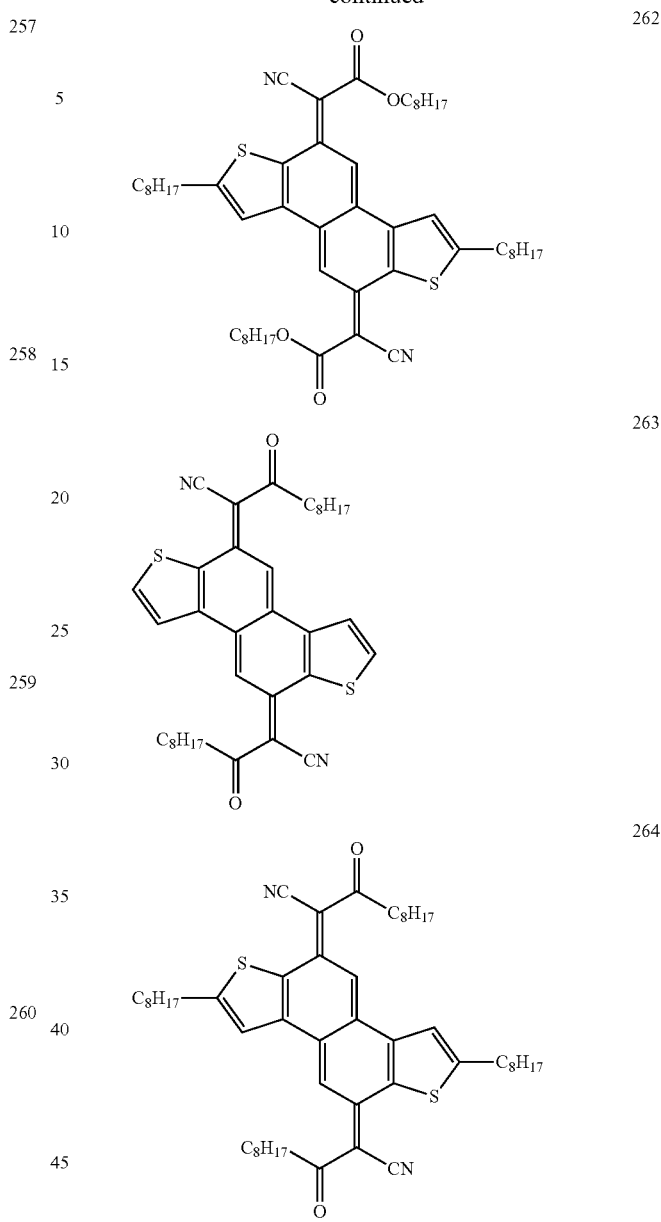

An organic semiconductor composition according to the present invention is a solution or dispersion containing a fused polycyclic aromatic compound represented by general formula (1) or (2) in a solvent. The solvent is, although not particularly limited as long as a composition containing the compound therein can form a film on a substrate, preferably an organic solvent. The organic solvent can be used singly or in mixture of two or more thereof. The organic solvent includes halogenohydrocarbons such as dichloromethane, chloroform, and dichloroethane; ethers such as diethyl ether, anisole, and tetrahydrofuran; amides such as dimethylacetamide, dimethyformamide, and N-methylpyrrolidone; nitriles such as acetonitrile, propionitrile, and benzonitrile; alcohols such as methanol, ethanol, isopropanol, and butanol; fluorinated alcohols such as octafluoropentanol and pentafluoropropanol; esters such as ethyl acetate, butyl acetate, ethyl benzoate, and diethyl carbonate; aromatic hydrocarbons such as benzene, toluene, xylene, chlorobenzene, mesitylene, ethylbenzene, dichlorobenzene, chloronaphthalene, and tetrahydronaphthalene; and hydrocarbons such as hexane, cyclohexane, octane, decane, and tetralin.

The concentration of a fused polycyclic aromatic compound represented by general formula (1) or (2) in the organic semiconductor composition is, depending on the type of solvent and the thickness of a thin film to be formed, usually 0.001% by weight to 20% by weight and preferably 0.01% by weight to 10% by weight to the solvent. Also, in an organic semiconductor composition of the present invention, the compound is only required to be dissolved or dispersed in any of the above-described solvents, but preferably homogeneously dissolved.

A thin film can be formed by an organic semiconductor material containing a fused polycyclic aromatic compound represented by general formula (1) or (2) of the present invention. The thickness of the thin film is, depending on its applications, usually 0.1 nm to 10 μm, preferably 0.5 nm to 3 μm, and more preferably 1 nm to 1 μm.

The method for forming a thin film generally includes a method(s) used singly or in combination of two or more selected from the group consisting of vacuum processes such as resistance heating deposition, electron beam deposition, sputtering, and molecular stacking methods, solution processes such as spin coating methods, drop casting methods, dip coating methods, and spray methods, relief printing methods such as flexographic printing and resin relief printing, planographic printing methods such as offset lithography methods, dry offset lithography methods, and pad printing methods, intaglio printing methods such as gravure printing methods, stencil printing methods such as silk-screen printing methods, mimeograph printing methods, and lithographic printing methods, ink jet printing methods, and microcontact printing methods.

Among the above-described methods, a resistance heating deposition method is preferred as a vacuum process, and a spin coating method is preferred as a solution process.

Organic electronics devices can be fabricated by using a fused polycyclic aromatic compound represented by general formula (1) or (2) as a material for electronics applications. The organic electronics devices include thin film transistors, photoelectric conversion devices, organic solar cell devices, organic EL devices, organic light emitting transistor devices, and organic semiconductor laser devices. These will be described in detail.

First, thin film transistors will be described in detail.

A thin film transistor has two electrodes (a source electrode and a drain electrode) in contact with a semiconductor, and controls the current flowing between the electrodes by means of a voltage applied to another electrode called a gate electrode.

Generally, in a thin film transistor device, a structure in which the gate electrode is insulated with an insulating film (Metal-Insulator-Semiconductor MIS structure) is often used. A structure in which a metal oxide film is used as the insulating film is called an MOS structure. In addition, a structure in which the gate electrode is formed via a shot key barrier (that is, an MES structure) is available, but the MIS structure is often used for a thin film transistor using an organic semiconductor material.

A thin film transistor to be fabricated by using an organic semiconductor material will be described more in detail with reference to drawings hereinbelow, but the present invention is not limited to these structures.

FIG. 1 shows some exemplary aspects of a thin film transistor (device).

In each exemplary aspect shown in FIG. 1, reference numeral 1 denotes a source electrode, reference numeral 2 denotes a semiconductor layer, reference numeral 3 denotes a drain electrode, reference numeral 4 denotes an insulator layer, reference numeral 5 denotes a gate electrode, and reference numeral 6 denotes a substrate, respectively. It should be noted that the arrangement of each layer and electrode can be selected as appropriate depending on the applications of the device. A to D, and F, in which the current flows in a direction parallel to the substrate, are called a lateral transistor. A is called a bottom-contact and bottom gate structure, and B is called a top-contact and bottom-gate structure. Also, C is provided with a source electrode and a drain electrode as well as an insulator layer on a semiconductor, and additionally forms a gate electrode thereon, being called a top-contact and top gate structure. D has a structure called a top and bottom contact and bottom gate transistor. F is a bottom-contact and top-gate structure. E is a schematic diagram of a transistor having a longitudinal structure, or a static induction transistor (SIT). This SIT spreads the current flow in a plane, enabling a large number of carriers to be moved at a time. Also, since the distance between the electrodes can be reduced due to the longitudinal arrangement of the source electrode and the drain electrode, the response is fast. Thus, the SIT can be preferably used in applications for allowing a large amount of current to flow and for switching at high speed. It should be noted that, although a substrate is not drawn in E of FIG. 1, a substrate is usually provided external of the source or drain electrode represented by 1 and 3 in E of FIG. 1.

Each component in each exemplary aspect will be described.

It is necessary for the substrate 6 to hold each layer to be formed thereon without delaminating. The substrate 6 can be fabricated from insulating materials such as resin plates or films, paper, glass, quartz, and ceramics, by forming an insulating layer on a conductive base material such as metals and alloys using coating and the like, or from combinations of two or more materials such as resins and inorganic materials. The resin plates or films can be fabricated from, for example, polyethylene terephthalate, polyethylene naphthalate, polyether sulfone, polyamide, polyimide, polycarbonate, cellulose triacetate, and polyetherimide. Use of resin films and paper can provide flexible and light-weight devices and enhances the practical utility. The thickness of the substrate is usually 1 μm to 10 mm and preferably 5 μm to 5 mm.

In the source electrode 1, the drain electrode 3, and the gate electrode 5, materials having electrical conductivity are used. For example, metals such as platinum, gold, silver, aluminum, chromium, tungsten, tantalum, nickel, cobalt, copper, iron, lead, tin, titanium, indium, palladium, molybdenum, magnesium, calcium, barium, lithium, potassium, and sodium and alloys containing thereof; conductive oxides such as $InO_2$, $ZnO_2$, $SnO_2$, and ITO; conductive polymer compounds such as polyaniline, polypyrrole, polythiophene, polyacetylene, polyparaphenylene, vinylene, and polydiacetylene; semiconductors such as silicon, germanium, and gallium arsenide; carbon materials such as carbon black, fullerenes, carbon nanotubes, graphite, and graphene can be used. Also, the conductive polymer compounds and semiconductors may be doped. Examples of a dopant include inorganic acid such as hydrochloric acid and sulfuric acid; organic acids having an acidic functional group such as sulfonic acid; Lewis acids such as $PF_5$, $AsF_5$, and $FeCl_3$; halogen atoms such as iodine; and metal atoms such as lithium, sodium, and potassium. Boron, phosphorous, arsenic, and the like are also frequently used as a dopant for inorganic semiconductors such as silicon.

Also, conductive composite materials obtained by dispersing carbon black, metal particles, and the like in the above-described dopants are used. In order to reduce the contact resistance of the source electrode 1 and the drain electrode 3, which are to be in direct contact with the semiconductor, it is important to select an appropriate work function or to treat surfaces.

Also, the distance between the source electrode and the drain electrode (the channel length) is a key factor to determine the characteristics of the device. The channel length is usually 0.01 to 300 µm and preferably 0.1 to 100 µm. The shorter the channel length, the larger the amount of current can be obtained. However, in contrast, short channel effects such as influences from contact resistance are caused, making control difficult. Thus, a proper channel length is required. The width between the source electrode and the drain electrode (the channel width) will be usually 10 to 10000 µm and preferably 100 to 5000 µm. Also, it is possible to form a channel having a larger width by allowing the electrodes to have a comb-like structure and the like. Depending on the amount of current required, the structure of the device, and the like, it is necessary to adjust the width to an appropriate length.

Each structure (shape) of the source electrode and the drain electrode will be described. Each structure of the source electrode and the drain electrode may be the same or different.

In the case of the bottom-contact structure, each electrode is fabricated generally by using a lithography method, and also each electrode is preferably formed into a rectangle. Printing precision in various printing methods has been enhanced recently, and precise fabrication of electrodes by using techniques such as inkjet printing, gravure printing, or screen printing has been enabled. In the case of the top contact structure, in which electrodes are mounted on a semiconductor, deposition can be made using a shadow mask and the like. Direct printing and formation of electrode patterns has been also enabled by using techniques such as inkjet. The length of the electrodes is the same as the aforementioned channel width. The width of the electrodes is, although not particularly specified, preferably smaller in order to reduce the area of the device within an extent that the electric characteristics can be stabilized. The width of the electrodes is usually 0.1 to 1000 µm and preferably 0.5 to 100 µm. The thickness of the electrode is usually 0.1 to 1000 nm, preferably 1 to 500 nm, and more preferably 5 to 200 nm. The electrodes 1, 3, and 5 are each connected with wiring, which is fabricated of a material substantially same as the electrodes.

As the insulator layer 4, materials having insulation characteristics are used. Examples of the material that may be used include polymers such as polyparaxylylene, polyacrylate, polymethyl methacrylate, polystyrene, polyvinyl phenol, polyamide, polyimide, polycarbonate, polyester, polyvinyl alcohol, polyvinyl acetate, polyurethane, polysulfone, fluorine resins, epoxy resins, and phenol resins and copolymers by combination of these; metal oxides such as silicon dioxide, aluminum oxide, titanium oxide, and tantalum oxide; ferroelectric metal oxides such as $SrTiO_3$ and $BaTiO_3$; dielectrics, such as nitrides such as silicon nitride and aluminum nitride, sulfides, and fluorides; or polymers in which particles of these dielectrics are dispersed. This insulator layer preferably has high electrical insulation characteristics in order to reduce leak current. This can decrease the film thickness thereby to increase the insulation capacity, increasing the amount of current to be obtained. Also, to enhance the mobility in a semiconductor, it is preferred that the surface energy on the surface of the insulator layer be decreased and that the film be smooth without asperities. Thus, in some cases, a self-assembled monolayer and a double insulator layer may be formed. The film thickness of the insulator layer 4 is, although depending on materials, usually 0.1 nm to 100 µm, preferably 0.5 nm to 50 µm, and more preferably 1 nm to 10 µm.

The fused polycyclic aromatic compound represented by the general formula (1) or (2) of the present invention can be used as a material of the semiconductor layer 2. This compound is formed using the method previously shown into the semiconductor layer 2 as a thin film. For the purpose of improving the characteristics of the thin film transistor, imparting other characteristics, and the like, other organic semiconductor materials and various additives can be mixed as required.

In thin film transistors, at least one compound of the fused polycyclic aromatic compounds represented by the above-described general formula (1) or (2) can be used as an organic semiconductor material. In the case where a thin film of a compound represented by the general formula (1) or (2) is formed via a solution process, that is, in the case where a solvent is used, the thin film is preferably used after the solvent is substantially evaporated. It is preferred to form a thin film from the organic semiconductor material in a deposition method which is a dry process.

For the purpose of improving characteristics of transistors and the like, additives such as dopants can be contained. The additives are added usually in a range of 0.01 to 10% by weight, preferably 0.05 to 5% by weight, and more preferably 0.1 to 3% by weight, based on the total amount of the organic semiconductor material.

The semiconductor layer may be formed with a plurality of layers, but is more preferably a single layer structure. The film thickness of the semiconductor layer 2 is preferably as thin as possible to the extent that the necessary functions are not eliminated. In lateral thin film transistors as shown in A, B, and D, that is because a larger film thickness often increases leak current, although the characteristics of the device do not depend on the film thickness if the thickness of the film is larger than specified. The film thickness of the semiconductor layer to exhibit necessary functions is usually 1 nm to 1 µm, preferably 5 nm to 500 nm, and more preferably 10 nm to 300 nm.

On a thin film transistor, other layer can be provided, for example, between the substrate layer and the insulating film layer, between the insulating film layer and the semiconductor layer, or on the exterior of the device, as required. For example, formation of a protective layer directly or via other layer on an organic semiconductor layer can diminish outside air influences such as humidity. Also, there exists an advantage to stabilize electric characteristics, such as an ability to increase the ON/OFF ratio of the thin film transistor device.

As the above-described protective layer, although not particularly limited, for example, films made from various resins such as epoxy resins, acrylic resins such as polymethyl methacrylate, polyurethane, polyimide, polyvinyl alcohol, fluorine resins, and polyolefins; inorganic oxide films such as silicon oxide, aluminum oxide, and silicon nitride; and films made of dielectrics such as nitride films are preferably used. Particularly, resins (polymers) having a small permeability of oxygen and moisture and a small water-absorbing ratio. Gas-barrier protective materials developed for organic EL displays can be used. The film thickness of the protective layer is, although any film thickness can be selected depending on the purpose, usually 100 nm to 1 mm.

Also, preliminary surface modifications or surface treatments are performed on a substrate or an insulator layer on which an organic semiconductor layer is to be stacked, enabling the characteristics as a thin film transistor device to be improved. Adjustment of the degree of hydrophilicity/hydrophobicity of the substrate surface, for example, can improve the quality of a film to be deposited on the substrate and the film deposition ability. Particularly, organic semiconductor materials may largely change in the characteristics depending on the film conditions such as molecular orientation. Thus, it is conceivable that surface treatments to the substrate, the insulator layer, and the like control molecular orientation in the interface portion between the substrate and an organic semiconductor layer subsequently to be deposited or reduce trap sites on the substrate and the insulator layer, leading to improvement of the characteristics such as carrier mobility.

A trap site refers to a functional group, such as a hydroxyl group, present on an untreated substrate. If such a functional group is present, electrons are attracted to the functional group, and, as the result, the carrier mobility is decreased. Accordingly, decreases in trap sites may be often effective for improving characteristics such as carrier mobility.

Examples of the surface treatment to improve characteristics as above described include one treatment or two or more treatments in combination selected from the group consisting of self-assembled monolayer treatments with hexamethyldisilazane, octyltrichlorosilane, and octadecyltrichlorosilane; surface treatments with polymers; acid treatments with hydrochloric acid, sulfuric acid, and acetic acid; alkaline treatment with sodium hydroxide, potassium hydroxide, calcium hydroxide, and ammonia; ozone treatments; fluorination treatment; plasma treatments with oxygen and argon; treatments for forming Langmuir-Blodgett films; treatments for forming thin films of other insulators and semiconductors; mechanical treatments; electric treatments such as corona discharge; and rubbing treatments by use of fibers.

Subsequently, the method for producing a thin film transistor device according to the present invention will be described below based on FIG. 2, using the top contact-bottom gate type thin film transistor shown in the exemplary aspect B of FIG. 1 as an example. This production method is applicable in the same way to thin film transistors of other aspects described above.

(Thin Film Transistor Substrate and Substrate Treatments)

Figure 2:
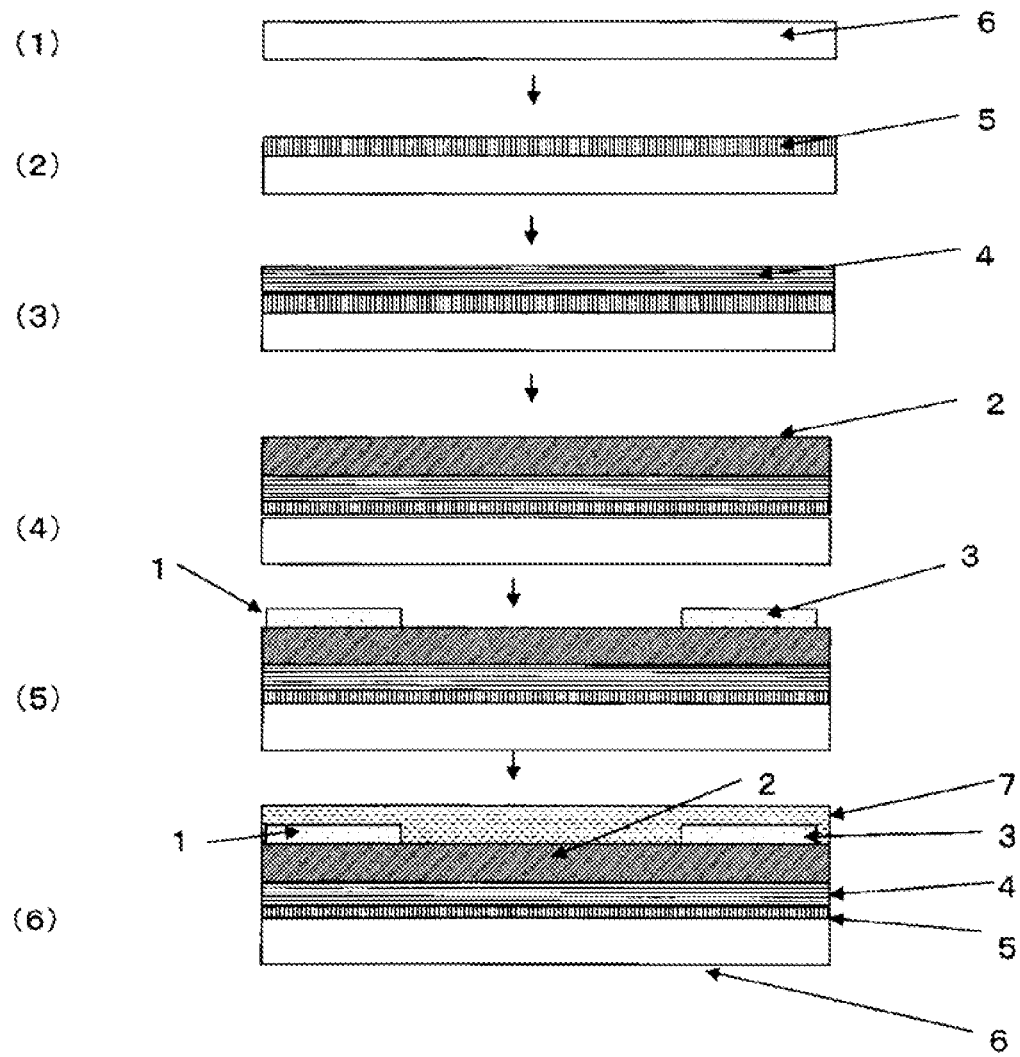
FIG. 2 is a schematic view of a step of producing a thin film transistor according to one exemplary aspect of the present invention.

The thin film transistor of the present invention is fabricated by mounting various layers and electrodes required on a substrate 6 (see FIG. 2 (1)). As the substrate, those described above can be used. The previously-described surface treatments and the like can be performed to this substrate. The thickness of the substrate 6 is preferably thin to the extent that the necessary functions are not impaired. Although depending on materials, the thickness is usually 1 μm to 10 mm and preferably 5 μm to 5 mm. Also, it is possible to allow the substrate to have the functions of the electrode, as required.

(Gate Electrode Formation)

A gate electrode 5 is formed on the substrate 6 (see FIG. 2 (2)). As the electrode material, those described above can be used. As a method for depositing an electrode film, various methods can be used. For example, a vacuum deposition method, a sputtering method, an application method, a heat transfer method, a printing method, and a sol-gel method can be adopted. During or after film deposition, patterning is preferably performed as required so as to achieve the desired configuration. As a method for patterning, various methods may also be used. Examples of the method include a photolithography method, in which patterning with photoresist and etching are combined. Also, patterning is enabled by making use of a deposition method using a shadow mask, a sputtering method, printing methods such as inkjet printing, screen printing, offset printing, and relief printing, soft lithography techniques such as microcontact printing methods and techniques combining a plurality thereof. The film thickness of the gate electrode 5, although depending on materials, is usually 0.1 nm to 10 μm, preferably 0.5 nm to 5 μm, and more preferably 1 nm to 3 μm. Also, if the gate electrode also serves as a substrate, the film thickness may be greater than the above-described film thickness.

(Insulator Layer Formation)

An insulator layer 4 is formed on the gate electrode 5 (see FIG. 2 (3)). As the insulator material, those described above can be used. On forming the insulator layer 4, various methods may be used. Examples of the method include application methods such as spin coating, spray coating, dip coating, cast, bar coat, and blade coating, printing methods such as screen printing, offset printing, and inkjet, and dry process methods such as vacuum deposition methods, molecular beam epitaxy methods, ion cluster beam methods, ion plating methods, sputtering methods, atmospheric-pressure plasma methods, and CVD methods. Additionally, sol-gel methods and methods for forming an oxide film, such as on metal, such as alumite on aluminum and silicon dioxide on silicon, with a thermal oxidation method and the like are to be adopted. It should be noted that, at the portion where the insulator layer comes in contact with the semiconductor layer, the insulator layer can be subjected to a predetermined surface treatment in order to allow molecules constituting the semiconductor, for example, molecules of the compound represented by the above-described formula (1) to be well oriented on the interface between both layers. The surface treatment technique that is the same as the surface treatments for the substrate may be used. The film thickness of the insulator layer 4 is preferably as thin as possible because a rise in the electric capacity can increase the amount of electricity to be obtained. At this point, leak current is increased in a thinner film, thus the film is preferably as thin as possible to the extent that the functions are not impaired. The thickness is usually 0.1 nm to 100 μm, preferably 0.5 nm to 50 μm, and more preferably 5 nm to 10 μm.

(Organic Semiconductor Layer Formation)

An organic semiconductor material containing the fused polycyclic aromatic compound represented by the above-described general formula (1) or (2) of the present invention is used for forming an organic semiconductor layer (see FIG. 2 (4)). On depositing an organic semiconductor layer, various methods can be used. Examples of the method specifically include vacuum-process forming methods via vacuum processes such as sputtering methods, CVD methods, molecular beam epitaxy methods, and vacuum deposition methods; application methods such as dip coat methods, die coater methods, roll coater methods, bar coater methods, and spin coat methods; forming methods via solution processes such as inkjet methods, screen printing methods, offset printing methods, and microcontact printing methods.

First, a method for depositing an organic semiconductor material via a vacuum process to thereby obtain an organic semiconductor layer will be described. As the film deposition method via a vacuum process, a method for heating the aforementioned organic semiconductor material in a crucible or an metal boat under vacuum to thereby attach (deposit) the evaporated organic semiconductor material on a target (a substrate, an insulator layer, a source electrode, a drain electrode, and the like), that is, a vacuum deposition method is preferably adopted. In this case, the degree of vacuum is usually $1.0 \times 10^{-1}$ Pa or less and preferably $1.0 \times 10^{-3}$ Pa or less. Also, since the characteristics of the organic semiconductor film, and thereby those of the thin film transistor may change depending on the substrate temperature during deposition, it is preferred that the substrate temperature be carefully selected. The temperature of the substrate during deposition is usually 0 to 200° C., preferably 5 to 180° C., more preferably 10 to 150° C., even more preferably 15 to 120° C., and particularly preferably 20 to 100° C.

Also, the deposition rate is usually 0.001 nm/second to 10 nm/second and preferably 0.01 nm/second to 1 nm/second. The film thickness of an organic semiconductor layer to be formed from the organic semiconductor material is usually 1 nm to 1 µm, preferably 5 nm to 500 nm, and more preferably 10 nm to 300 nm.

It should be noted that some other techniques may be used instead of the deposition method wherein an organic semiconductor material for forming an organic semiconductor layer is heated, evaporated, and attached onto a target.

Subsequently, a method for depositing a film via a solution process to thereby obtain an organic semiconductor layer will be described. The fused polycyclic aromatic compound represented by the general formula (1) or (2) of the present invention is dissolved in a solvent and the like, to which additives and the like are added if necessary. The composition thus obtained is applied to a target (exposed portions of the insulator layer, the source electrode, and the drain electrode). Examples of the application method include coating methods such as casting, spin coating, dip coating, blade coating, wire bar coating, and spray coating, printing methods such as inkjet printing, screen printing, offset printing, flexo printing, and relief printing, or soft lithography techniques such as microcontact printing methods, or methods in which a plurality of these techniques are combined.

Furthermore, as methods similar to the application method, the Langmuir project method, wherein the above-described composition is added dropwise on a water surface to fabricate an organic semiconductor monolayer, and the monolayer is transferred to the substrate for stacking, and a method for introducing a material in a liquid-crystal or melt state between two substrates using capillarity can be adopted.

The environment such as the temperature of the substrate and the composition during deposition is important. Since the characteristics of the transistor may change depending on the temperature of the substrate and the composition, it is preferred that the temperature of the substrate and the composition be carefully selected. The temperature of the substrate is usually 0 to 200° C., preferably 10 to 120° C., more preferably 15 to 100° C. Also, since the characteristics of the transistor are largely dependent on solvents and the like in the composition used, attention has to be paid.

The film thickness of the organic semiconductor layer fabricated by this method is preferably smaller to the extent that the functions are not impaired. There is a concern that the larger film thickness increases the leak current. The film thickness of the organic semiconductor layer is usually 1 nm to 1 µm, preferably 5 nm to 500 nm, and more preferably 10 nm to 300 nm.

It is possible to further improve the characteristics of the organic semiconductor layer thus formed (see FIG. 2 (4)) via a post-treatment. For example, since a heat treatment can lessen distortion of the film generated during deposition, reduce pin holes and the like, and control the arrangement and orientation in the film, it is possible to promote improvement and stabilization of characteristics of the organic semiconductor. This heat treatment is effectively performed to improve the characteristics on fabricating the thin film transistor of the present invention. The heat treatment is performed by heating the substrate after the organic semiconductor layer is formed. The temperature of the heat treatment is, although not particularly limited, usually from room temperature to of the order of 150° C., preferably 40 to 120° C., and more preferably 45 to 100° C. The heat treatment time is, although not particularly limited, usually from 10 seconds to 24 hours and preferably from 30 seconds to of the order of 3 hours. The heat treatment may be performed under the air atmosphere, or under inert atmosphere such as nitrogen and argon. Additionally, solvent vapors can control film configurations.

Examples of other post-treatments of the organic semiconductor layer include treatments for inducing changes in characteristics via oxidization or reduction by treating the organic semiconductor layer using oxidizing or reducing gases such as oxygen and hydrogen and oxidizing or reducing liquids. This can be used for the purpose of increasing or reducing the carrier density in the film.

A technique called doping can also change the characteristics of an organic semiconductor layer by addition of a trace amount of elements, atom groups, molecules, or polymers to the organic semiconductor layer. The organic semiconductor layer can be doped with, for example, oxygen, hydrogen, acids such as hydrochloric acid, sulfuric acid, and sulfonic acid; Lewis acids such as $PF_5$, $AsF_5$, and $FeCl_3$; halogen atoms such as iodine; and metal atoms such as sodium and potassium; donor compounds such as TTF and phthalocyanine. This can be achieved by bringing the organic semiconductor layer into contact with these gases, immersing the layer in a solution, or subjecting the layer to an electrochemical doping treatment. These doping treatments can be performed not only after fabrication of the organic semiconductor layer but also during synthesis of the organic semiconductor compound. In a process of forming an organic semiconductor layer by using a composition, the aforementioned dopant can be added to the composition, or also at the stage of forming a thin film, the aforementioned dopant can be added. Doping can be achieved also by adding the aforementioned dopant to materials for forming the organic semiconductor layer during vapor deposition to thereby perform co-deposition, by mixing the dopant into the surrounding atmosphere during fabrication of the organic semiconductor layer (that is, the organic semiconductor layer is fabricated in the presence of the aforementioned dopant), and furthermore, by accelerating ions of the dopant in vacuum to thereby allow the ions to collide on the film.

Examples of effects of these doping treatments include changes in the electric conductivity due to the increased or decreased carrier density, changes in the carrier polarity reversal (p-type or n-type), and changes in the Fermi level.

(Source Electrode and Drain Electrode Formation)

The source electrode 1 and the drain electrode 3 can be formed in accordance with the case of the gate electrode 5

(see FIG. 2 (5)). Also, various additives can be used to reduce the contact resistance with the organic semiconductor layer.

(Protective Layer)

Formation of a protective layer 7 on the organic semiconductor layer has advantages of minimizing outside air influences and also, of stabilizing the electric characteristics of the organic thin film transistor (see FIG. 2 (6)). As materials of the protective layer, the aforesaid materials are used. The film thickness of the protective layer 7 is, although any film thickness can be adopted depending on the purpose, usually 100 nm to 1 mm.

On depositing the protective layer, various methods can be adopted. In the case where the protective layer is composed of a resin, examples of the method include methods for applying a resin solution to thereby dry the solution to form a resin film; and methods for applying or vapor depositing a resin monomer to thereby polymerize the monomer. Crosslinking treatments may be performed after layer deposition. In the case where the protective layer is composed of inorganic materials, for example, forming methods via vacuum processes such as a sputtering method and a vapor deposition method, or forming methods via solution processes such as a sol-gel method also can be used.

In the case of a thin film transistor, a protective layer can be provided not only on the organic semiconductor layer, but also between each layer as required. These protective layers may serve to stabilize the electric characteristics of the thin film transistor.

Since the fused polycyclic aromatic compound represented by the above-described general formula (1) or (2) is used as an organic semiconductor material, thin film transistors can be produced in a relatively low-temperature process. Thus, flexible materials which could not be used under high-temperature exposure conditions, such as plastic plates and plastic films, can be used as a substrate. As the result, production of light-weight, highly flexible, and hardly breakable devices has been enabled. The devices can be utilized as switching devices and the like for active matrices in displays.

Thin film transistors also can be utilized as digital devices or analog devices such as memory circuit devices, signal driver circuit devices, and signal processing circuit devices. Furthermore, these devices can be combined to fabricate displays, IC cards, IC tags, and the like. Furthermore, thin film transistors, which can cause changes in their characteristics with external stimuli such as chemical substances, can be also used as an FET sensor.

Subsequently, organic EL devices will be described.

Organic EL devices have attracted attention due to their applicability to uses such as solid-state and self-luminous large area color display and illumination, and a large number of their developments have been conducted. The structures such as a structure having two layers, an emitting layer and a charge transport layer, between opposing electrodes composed of a cathode and an anode; a structure having three layers, an electron transport layer, an emitting layer, and hole transport layer, stacked between opposing electrodes; and a structure having three or more layers are known, and a structure having only a single emitting layer is also known.

The fused polycyclic aromatic compound represented by the above-described general formula (1) or (2) can be used as the above-described electron transport layer, emitting layer, and hole transport layer.

(Photoelectric Conversion Device)

Utilization of semiconductor characteristics of the fused polycyclic aromatic compound represented by the general formula (1) or (2) of the present invention enables the compound to be utilized for organic photoelectric conversion devices. Examples of the photoelectric conversion device include charge-coupled devices (CCD) that convert video signals such as moving and still images into digital signals as an image sensor, which is an solid state image sensor. The photoelectric conversion device is also expected to be utilized in organic photoelectric conversion devices by making use of its more inexpensiveness, large area processability, and flexible functionality unique to organic materials.

(Organic Solar Cell Device)

The fused polycyclic aromatic compound represented by the general formula (1) or (2) of the present invention is used to thereby enable flexible and low-cost organic solar cell devices to be easily fabricated. That is, organic solar cell devices features advantages of flexibility and extended life because of being solid-state devices. Conventionally, solar cells using organic thin film semiconductors in combination with conductive polymers and fullerenes have been mainly developed, but their power generation conversion efficiency is posing a problem.

Generally, in the structure of an organic solar cell device, similarly to silicon solar cells, a layer that generates power (power generation layer) is interposed between an anode and a cathode. The device absorbs light to generate holes and electrons, which are received by each electrode, to thereby function as a solar cell. The power generation layer is composed of a P-type donor material, an N-type acceptor material, and other materials such as a buffer layer. Solar cells in which organic materials are used as these materials are called organic solar cells.

Figure 3:
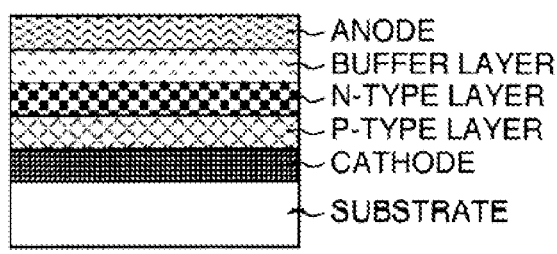
FIG. 3 is a schematic view of a structure in photoelectric conversion devices and solar cells.

Examples of the structure include Schottky barrier junctions, hetero junctions, bulk-hetero junctions, nanostructured junctions, and hybrids. The materials each effectively absorb incident light, generate electric charges, and separate, transport, and collect the generated electric charges (holes and electrons) to thereby function as a solar cell. It should be noted that one exemplary structure of a hetero junction device, which is a structure of a common solar cell, is shown in FIG. 3.

Then, components in an organic solar cell device will be described.

An anode and a cathode in the organic solar cell device are the same as in the organic EL device previously mentioned. The electrodes desirably have transparency in the absorption wavelength region of the power generation layer because they have to efficiently absorb light. Additionally, in order to have good solar cell characteristics, the solar cell preferably has a sheet resistance of $20\Omega/\square$ or less and a light permeability of 85% or more.

The power generation layer is formed by one or more organic thin layers containing at least the compound represented by the general formula (1) or (2) of the present invention. Although able to have a structure previously shown, an organic solar cell device is basically composed of a P-type donor material, an N-type acceptor material, and a buffer layer.

Examples of the p-type donor material include compounds capable of transporting holes as in the case of hole injection and hole transport layers basically described in the organic EL device section, π-conjugated polymers such as polyparaphenylene vinylene derivatives, polythiophene derivatives, polyfluorene derivatives, and polyaniline derivatives, and polymers having carbazole and other hetero rings in the side chain. The examples also include low molecular weight compounds such as pentacene derivatives, rubrene derivatives, porphyrin derivatives, phthalocyanine derivatives, indigo derivatives, quinacridone derivatives, merocyanine derivatives, cyanine derivatives, squarylium derivatives, and benzoquinone derivatives.

The fused polycyclic aromatic compound of the general formula (1) or (2) of the present invention can be suitably used as an n-type acceptor material. This acceptor material can be used singly, but also can be used in mixture with other acceptor materials. Examples of the acceptor materials to be mixed include compounds capable of transporting electrons as in the case of electron transport layers basically described in the organic EL device section, oligomers and polymers having pyridine and derivatives thereof in the backbone, oligomers and polymers having quinoline and derivatives thereof in the backbone, polymers having benzophenanthrolines and derivatives thereof, polymer materials such as cyano-polyphenylene vinylene derivatives (such as CN-PPV), and low molecular weight materials such as fluorinated phthalocyanine derivatives, perylene derivatives, naphthalene derivatives, bathocuproine derivatives, and fullerene derivatives such as C60, C70, and PCBM.

The acceptor materials each preferably absorb light efficiently and generate electric charges. Those in which materials having a high absorbance coefficient are used are preferred.

The method for forming a thin film for the power generation layer of the organic solar cell is as the method described in the organic EL device section previously described. The film thickness of the thin film, although depending on the solar cell structure, is preferably thicker in order to sufficiently absorb light and to prevent short circuits. In contrast, the distance to transport generated electric charges is preferably shorter, and thus, the thinner thickness is suitable. In general, the thickness of the power generation layer is preferably from 10 to of the order of 500 nm.

(Organic Semiconductor Laser Device)

The fused polycyclic aromatic compound represented by the general formula (1) or (2) of the present invention, which is a compound having organic semiconductor characteristics, is expected to be used as organic semiconductor laser devices. That is, into the organic semiconductor device including the compound represented by the general formula (1) or (2) of the present invention, a resonator structure is integrated. If efficient carrier injection can sufficiently increase the excited state density, it is expected that the light is amplified to thereby lead to laser oscillation. Conventionally, only laser oscillation by light excitation is observed, and it is suggested that generation of a high-density excited state by injecting high density carriers, which are necessary for laser oscillation by electric excitation, into the organic semiconductor device is extremely difficult. Use of the organic semiconductor device containing the compound represented by the formula (1) or (2) of the present invention is expected to have a possibility of generating highly efficient light emission (electric field light emission).

EXAMPLES

Examples of the synthesis of fused polycyclic aromatic compounds represented by general formula (10) or general formula (11) are shown below.

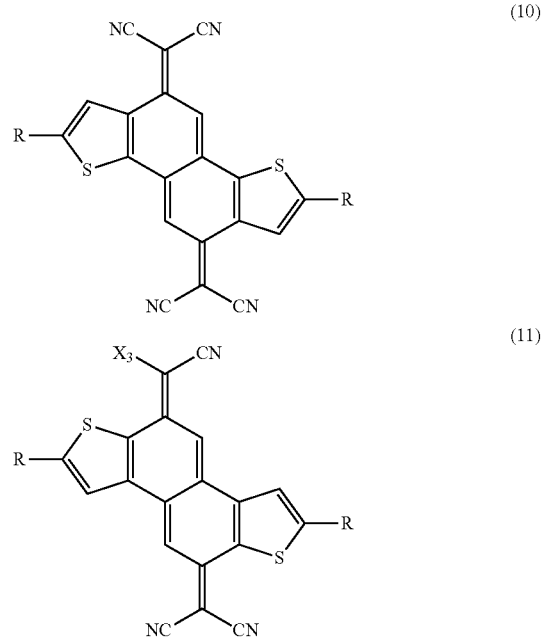

Fused polycyclic aromatic compounds represented by general formula (10) or general formula (11) was synthesized in accordance with the following process. In the process, dry distilled solvents were used for reactions and measurement under inert gases, and commercially available first- or special-grade solvents were used for other reactions and operations. Also, reagents were purified with dry distillation or the like as required, and in other cases, commercially available first- or special-grade reagents were used. Daiso Gel IR-60 (silica gel, active), MERCK Art 1097 Aluminiumoxide 90 (alumina, active) were used for column chromatography purification, and Silicagel 60F254 (MERCK) was used for TLC. Solvents were distilled off by a rotary evaporator. Analysis equipment and measurement equipment used are shown below.

Nuclear magnetic resonance spectrometry (referred to as "1H-NMR" hereinbelow) was conducted using a LAMBDA-NMR (395.75 MHz, σ value, ppm, Internal standard TMS). Mass spectrometry (referred to as "MS" hereinbelow) was conducted using a MALDI-MS KRATOS ANALYTICAL KOMPACT MALDI, Shimadzu GCMS-QP5050 mass spectrometer.

Example 1

To a 20 mL two-necked flask, malononitrile (0.9 mmol), THF (10 mL), and sodium hydride (2.1 mmol) were added and stirred for 30 minutes under a nitrogen atmosphere. Subsequently, 5,10-dibromo-naphtho[1,2-b:5,6-b']dithiophene (0.3 mmol) and Pd(PPh$_3$)$_4$ (0.07 mmol) were added and refluxed for 3 hours. After the reaction was completed, the mixture was left to cool to room temperature. A small amount of 1 N hydrochloric acid was added, and the precipitated solid was filtered off. Then, the obtained solid was dissolved in acetonitrile (5 mL), and bromine water was added. Subsequently, the precipitated solid was filtered off, thereby obtaining a compound 101 as a deep purple solid.

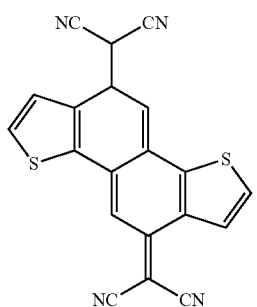

(101)

Compound 101 was obtained at a yield of 55%. Measurement results: 1H-NMR (400 MHz, CDCl₃) δ 7.71 (d, 2H), 7.81 (s, 2H), 8.43 (d, 2H).

Example 2

Except that 2,7-dioctyl-5,10-dibromo-naphtho[1,2-b:5,6-b']dithiophene was used instead of 5,10-dibromo-naphtho[1,2-b:5,6-b']dithiophene in Example 1, a process as in Example 1 was conducted, thereby obtaining Compound 110.

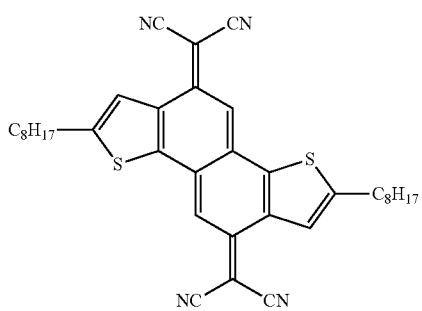

(110)

Compound 110 was obtained at a quantitative yield. Measurement results: ¹H-NMR (400 MHz, CDCl₃) δ 0.88 (t, 6H), 1.25-1.51 (m, 20H), 1.76 (Quin, 4H), 2.94 (t, 4H) 7.61 (s, 2H), 8.02 (s, 2H).

Example 3

Except that 2,7-didodecyl-5,10-dibromo-naphtho[1,2-b:5,6-b']dithiophene was used instead of 5,10-dibromo-naphtho[1,2-b:5,6-b']dithiophene in Example 1, a process as in Example 1 was conducted, thereby obtaining Compound 112.

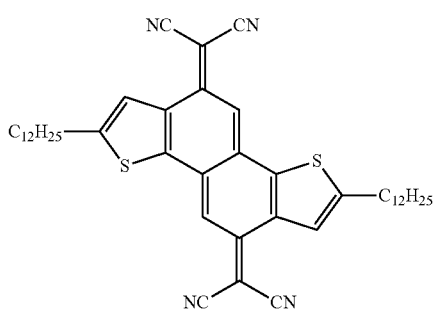

(112)

Compound 112 was obtained at a yield of 25%. Measurement results: ¹H-NMR (400 MHz, CDCl₃) δ 0.87 (t, 6H), 1.24-1.42 (m, 36H), 1.76 (Quin, 4H), 2.93 (t, 4H) 7.61 (s, 2H), 8.02 (s, 2H).

Example 4

Except that 2,7-bis(triisopropylsilyl)-5,10-dibromo-naphtho[1,2-b:5,6-b']dithiophene was used instead of 5,10-dibromo-naphtho[1,2-b:5,6-b']dithiophene in Example 1, a process as in Example 1 was conducted, thereby obtaining Compound 136.

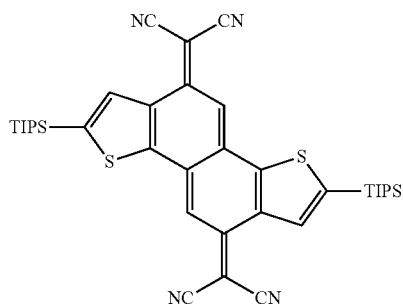

(136)

Compound 136 was obtained at a yield of 63%. Measurement results: ¹H-NMR (400 MHz, CDCl₃) δ 1.16 (d, 36H), 1.45 (sept, 6H), 7.80 (s, 2H), 8.53 (s, 2H).

Example 5

Except that 5,10-dibromo-naphtho[2,1-b:6,5-b']dithiophene was used instead of 5,10-dibromo-naphtho[1,2-b:5,6-b']dithiophene in Example 1, a process as in Example 1 was conducted, thereby obtaining Compound 201.

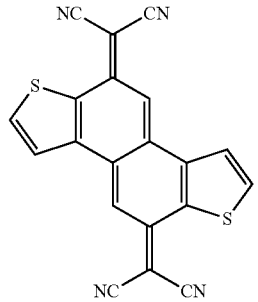

(201)

Compound 201 was obtained at a yield of 55%. Measurement results: ¹H-NMR (400 MHz, CDCl₃) δ 7.83 (d, 2H), 7.94 (d, 2H), 7.97 (s, 2H).

Example 6

Except that 2,7-dioctyl-5,10-dibromo-naphtho[2,1-b:6,5-b']dithiophene was used instead of 5,10-dibromo-naphtho[1,2-b:5,6-b']dithiophene in Example 1, a process as in Example 1 was conducted, thereby obtaining Compound 210.

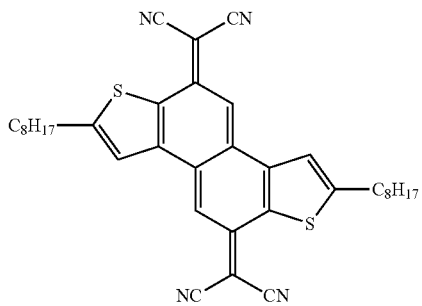

(210)

The compound 210 was obtained at a yield of 55%. Measurement results: $^1$H-NMR (400 MHz, CDCl$_3$) δ 0.87 (t, 6H), 1.24-1.42 (m, 20H), 1.79 (Quin, 4H), 2.97 (t, 4H) 7.45 (s, 2H), 7.81 (s, 2H).

Example 7

Except that 2,7-didodecyl-5,10-dibromo-naphtho [2,1-b:6,5-b']dithiophene was used instead of 5,10-dibromo-naphtho[1,2-b:5,6-b']dithiophene in Example 1, a process as in Example 1 was conducted, thereby obtaining Compound 212.

[Formula 28]

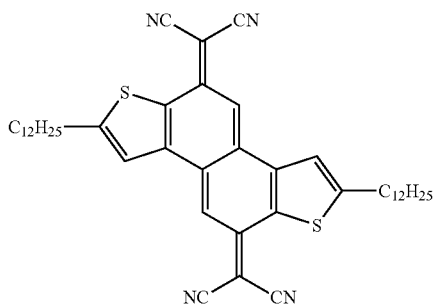

(212)

Compound 212 was obtained at a yield of 22%. Measurement results: $^1$H-NMR (400 MHz, CDCl$_3$) δ 0.87 (t, 6H), 1.24-1.42 (m, 36H), 1.79 (Quin, 4H), 2.97 (t, 4H) 7.45 (s, 2H), 7.81 (s, 2H).

Example 8

Except that 2,7-dihexadecyl-5,10-dibromo-naphtho[2,1-b:6,5-b']dithiophene was used instead of 5,10-dibromo-naphtho[1,2-b:5,6-b']dithiophene in Example 1, a process as in Example 1 was conducted, thereby obtaining Compound 214.

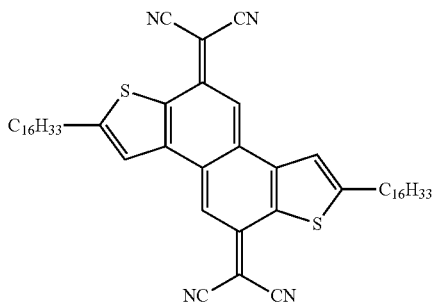

(214)

Compound 214 was obtained at a yield of 22%. Measurement results: $^1$H-NMR (400 MHz, CDCl$_3$) δ 0.87 (t, 6H), 1.24-1.42 (m, 52H), 1.79 (Quin, 4H), 2.97 (t, 4H) 7.45 (s, 2H), 7.81 (s, 2H).

Example 9

Except that 2,7-bis(triisopropylsilyl)-5,10-dibromo-naphtho[2,1-b:6,5-b']dithiophene was used instead of 5,10-dibromo-naphtho[1,2-b:5,6-b']dithiophene in Example 1, a process as in Example 1 was conducted, thereby obtaining Compound 236.

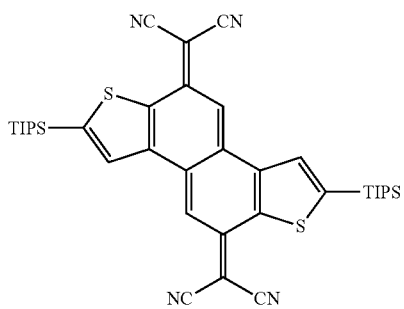

(236)

Compound 236 was obtained at a yield of 47%. Measurement results: $^1$H-NMR (400 MHz, CDCl$_3$) δ 1.18 (d, 36H), 1.47 (sept, 6H), 7.79 (s, 2H), 7.93 (s, 2H).

Evaluation of physical characteristics of fused polycyclic aromatic compounds (1) Solubility Measurement Solubility was measured by using chloroform as solvent. Table 3 shows the mass percent concentrations of Compound 110 and Compound 112 when saturated chloroform solutions thereof were prepared.

TABLE 3

|  | Solubility in chloroform (w/w %) |
|---|---|
| Compound 110 | 0.52 |
| Compound 112 | 0.22 |

(2) Electronic Absorption Spectrum (UV-Vis) Measurement

Figure 4:
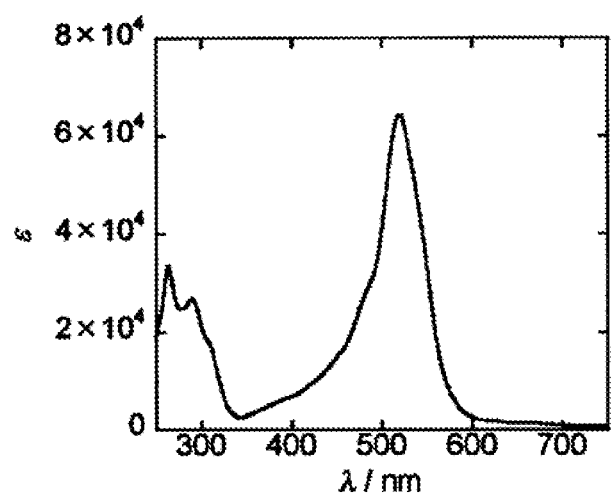
FIG. 4 is a graph showing the relationship between the electron absorption spectrum and the absorption wavelength of the compound 110 of the present invention.
Figure 5:
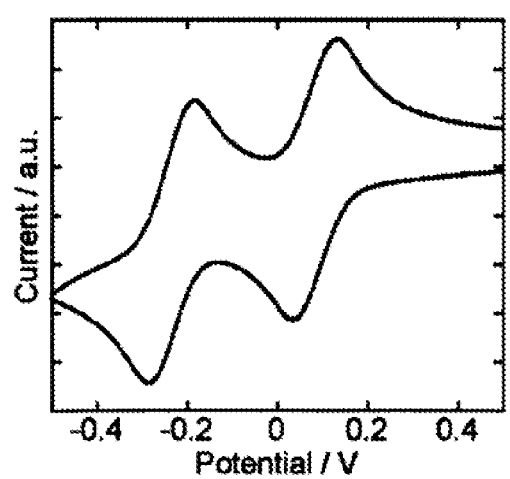
FIG. 5 is a graph showing a cyclic voltammogram of Compound 110 according to the present invention.
Figure 6:
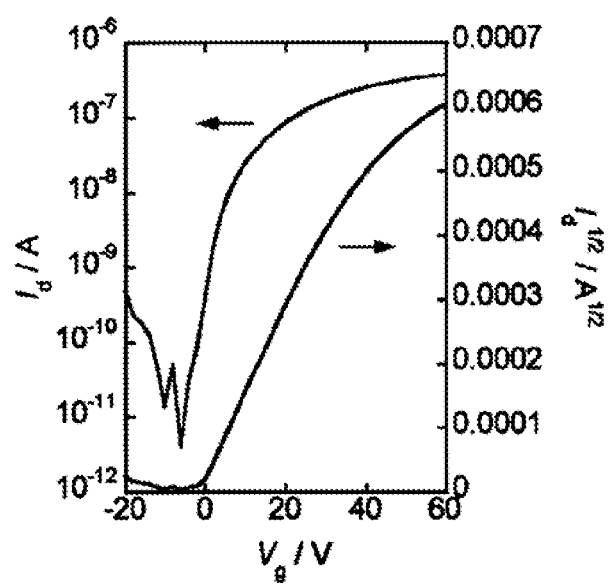
FIG. 6 is a graph showing the transmission characteristics of Compound 110 according to the present invention.

An electronic absorption spectrum was measured by using dichloromethane as solvent. FIG. 4 shows the relationship between the electronic absorption spectrum of Compound 110 (∈/M$^{-1}$cm$^{-1}$) and the absorption wavelength (λ/nm).

(3) CV (Cyclic Voltammetry) Measurement

CV measurement was conducted by using dichloromethane as solvent, tetrabutylammonium hexafluorophosphate (n-BuN$_4$PF$_6$, 0.1 M) as a supporting electrolyte, platinum wires as working electrodes and counter electrodes, and a silver-silver chloride electrodes as reference electrodes, and by sweeping the electric potential at a rate of 100 mV/sec. In all Compounds 101, 110, 112, 136, 201, 210, 212, 214, and 236, two pairs of oxidation-reduction waves were observed. The first half-wave reduction potentials were all 0.06 V and the second half-wave reduction potentials were −0.28 V, demonstrating that the compounds have high electron-acceptor ability.

(4) Evaluation of FET Characteristics

For evaluation of the FET characteristics of the above-described fused polycyclic aromatic compounds, FET devices were fabricated in accordance with the following process.

As for Compound 101, an organic thin film was formed on an n-doped silicon wafer having a SiO$_2$ thermal oxide film by vacuum deposition using a shadow mask.

As for Compounds 110 and 112, an organic thin film was formed on an n-doped silicon wafer having a SiO$_2$ thermal oxide film via a spin coat process.

Finally, a source-drain electrode was fabricated by vacuum-depositing Au on the organic thin films using a shadow mask. The FET devices fabricated have a channel length of 50 μm and a channel width of 1.5 mm. The FET devices thus fabricated are of a top-contact configuration. FIG. 1B shows the structure.

It should be noted that the thermal oxide film of the n-doped silicon wafer functions as an insulating layer (4) and that the n-doped silicon wafer functions as both of a substrate (6) and a gate electrode (5) in the field-effect transistor of this Example.

The performance of an FET device depends on the current that flows when an electric potential is applied among the source and the drain with an electric potential applied on the gate. The current can be measured to determine the mobility, which is the characteristic of a FET. The mobility can be calculated from expression (a) representing the electric characteristics of career species that generate in an organic semiconductor layer as the result of application of a gate electric field on SiO$_2$ as an insulator.

$$Id = Z\mu Ci(Vg-Vt)2/2L \quad (a)$$

Wherein, Id is the saturated source-drain current, Z is a channel width, Ci is the electric capacity of insulator, Vg is the gate voltage, Vt is the threshold electric potential, L is a channel length, and μ is the mobility to be determined (cm$^2$/Vs). Ci can be determined by the dielectric constant of a SiO$_2$ insulating film used, Z and L can be determined by the device structure of a FET device, Id and Vg can be determined when the current of a FET device is measured, and Vt can be determined from Id and Vd. Substitution of each value into the expression (a) enables the mobility at each gate voltage to be calculated.

FET characteristics of the Compound 101, Compound 110 and Compound 112 were evaluated in atmosphere by using the above formula. Table 4 shows the result of the FET characteristics.

TABLE 4

|  | Mobility (cm$^2$V$^{-1}$s$^{-1}$) | On/off ratio | Threshold voltage (V) |
|---|---|---|---|
| Compound 101 | 1.5 × 10$^{-2}$ | 10$^1$ | −18.9 |
| Compound 110 | 2.4 × 10$^3$ | 10$^3$ | 0.7 |
| Compound 112 | 2.4 × 10$^3$ | 10$^4$ | 1.2 |

INDUSTRIAL APPLICABILITY

As described above, according to the present invention, the solubility, conductivity, and electron mobility of fused polycyclic aromatic compounds and organic semiconductor materials can be enhanced, whereby provided are fused polycyclic aromatic compounds and organic semiconductor materials for which a solution approach can be employed and which enable stable n-type transistor operation even in the atmosphere. The present invention, therefore, can be applied to fields such as transistors, organic FET devices, diodes, capacitors, thin film photoelectric conversion devices, dye sensitized solar cells, thin film transistors (TFT), and light emitting devices having an organic carrier transport layer and/or emitting layer, and organic EL devices.

REFERENCE SIGNS LIST

In FIG. 1 to FIG. 3, the same numerals are assigned to the same names.
1 Source electrode
2 Semiconductor layer
3 Drain electrode
4 Insulator layer
5 Gate electrode
6 Substrate
7 Protective layer

The invention claimed is:
1. A fused polycyclic aromatic compound represented by general formula (1) or (2):

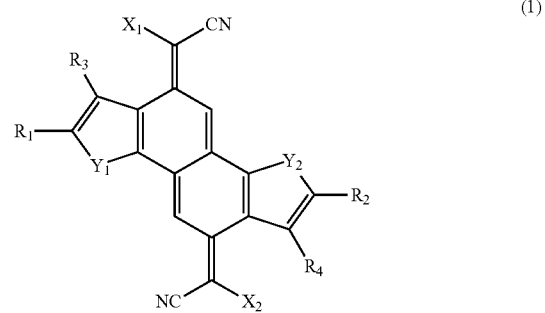

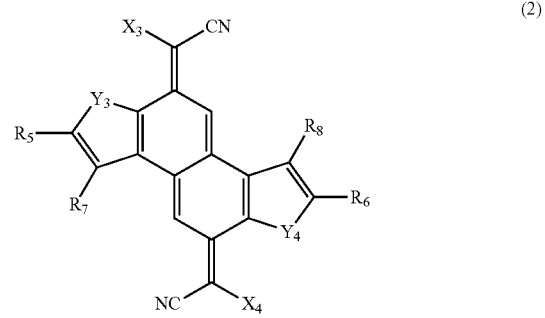

wherein $R_1$ to $R_8$ each independently represent an atom or a functional group selected from the group consisting of a hydrogen atom, a halogen atom, a hydrocarbon oxy group, an aromatic hydrocarbon group, an aliphatic hydrocarbon group, an alicyclic hydrocarbon group, an ester group, an acyl group, a cyano group, and a substituted silyl group, $X_1$ to $X_4$ each independently represent a cyano group, an ester group, or an acyl group, and $Y_1$, $Y_2$, $Y_3$ and $Y_4$ each independently represents a sulfur atom.

2. The fused polycyclic aromatic compound according to claim 1, wherein $X_1$, $X_2$, $X_3$ and $X_4$, each independently represents a cyano group.

3. The fused polycyclic aromatic compound according to claim 1, wherein $R_3$, $R_4$, $R_7$, and $R_8$ each independently represents a hydrogen atom.

4. The fused polycyclic aromatic compound according to claim 1 or 2, wherein $R_1$, $R_2$, $R_5$, and $R_6$ are each independently an aromatic hydrocarbon group or an aliphatic hydrocarbon group having 1 to 30 carbon atoms.

5. The fused polycyclic aromatic compound according to claim 4, wherein $R_1$, $R_2$, $R_5$, and $R_6$ are each independently a linear or branched chain alkyl group having 1 to 30 carbon atoms.

6. The fused polycyclic aromatic compound according to claim 1 or 2, wherein $R_1$, $R_2$, $R_5$, and $R_6$ are each independently a trimethylsilyl group, a triethylsilyl group, or a triisopropylsilyl group.

7. The fused polycyclic aromatic compound according to claim 1 or 2, wherein $R_1$, $R_2$, $R_5$, and $R_6$ each independently represents a hydrogen atom.

8. An organic semiconductor material comprising the fused polycyclic aromatic compound according to claim 1 or 2.

9. The organic semiconductor material according to claim 8, wherein the organic semiconductor material is an n-type semiconductor material.

10. A composition for forming an organic semiconductor comprising the fused polycyclic aromatic compound according to claim 1 or 2 and an organic solvent.

11. The composition for forming an organic semiconductor according to claim 10, wherein the content of the fused polycyclic aromatic compound is in a range of 0.01% by weight or more and 10% by weight or less relative to the total amount of the composition for forming an organic semiconductor.

12. A thin film comprising the fused polycyclic aromatic compound according to claim 1 or 2.

13. An organic semiconductor device comprising the thin film according to claim 12.

14. The organic semiconductor device according to claim 13, wherein the device is an organic transistor device.

15. A method for producing an organic semiconductor device comprising the step of depositing the fused polycyclic aromatic compound according to claim 1 or 2 on a substrate via a solution process.

16. A method for producing an organic semiconductor device comprising the step of depositing the fused polycyclic aromatic compound according to claim 1 or 2 on a substrate via a vacuum process.

* * * * *